US012624156B2

(12) United States Patent
Boyle et al.

(10) Patent No.: US 12,624,156 B2
(45) Date of Patent: *May 12, 2026

(54) PROCESSES FOR FORMING EPOXY RESIN COMPOSITIONS AND SEPARATION PROCESSES

(71) Applicant: Westlake Epoxy Inc., Houston, TX (US)

(72) Inventors: Nicola Majella Boyle, Rotterdam (NL); Jimmy Antonius Van Rijn, The Hague (NL); Maria Santana Martin, Amsterdam (NL)

(73) Assignee: Westlake Epoxy Inc., Houston, TX (US)

( * ) Notice: Subject to any disclaimer, the term of this patent is extended or adjusted under 35 U.S.C. 154(b) by 674 days.

This patent is subject to a terminal disclaimer.

(21) Appl. No.: 18/130,876

(22) Filed: Apr. 4, 2023

(65) Prior Publication Data

US 2024/0336722 A1 Oct. 10, 2024

(51) Int. Cl.

*C08G 59/06* (2006.01)
*C07D 301/28* (2006.01)
*C08G 59/02* (2006.01)

(52) U.S. Cl.

CPC ......... *C08G 59/063* (2013.01); *C07D 301/28* (2013.01); *C08G 59/022* (2013.01)

(58) Field of Classification Search

None

See application file for complete search history.

(56) References Cited

U.S. PATENT DOCUMENTS 3,984,363 A 10/1976 D'Alelio
8,461,286 B2 6/2013 Young et al.

(Continued)

FOREIGN PATENT DOCUMENTS

CN 103140533 A 6/2013
CN 104861670 A * 8/2015
CN 113717400 A * 11/2021 ............... C08H 6/00

OTHER PUBLICATIONS

International Search Report dated Jul. 10, 2024 for Application No. PCT/US2024/021764.

(Continued)

*Primary Examiner* — Ha S Nguyen

(74) *Attorney, Agent, or Firm* — Patterson + Sheridan, LLP

(57) ABSTRACT

Embodiments of the present disclosure generally relate to processes for forming epoxy resin compositions and processes for separating substrates from complex mixtures. In an embodiment, a process for making an epoxy resin composition is provided and includes: reacting a mixture comprising a substrate, an epihalohydrin, and a catalyst to form a first composition comprising a halohydrin reaction product; introducing an alkaline reagent with the first composition to form a second composition comprising an epoxy resin product; introducing a liquid epoxy resin with the second composition to form a resin mixture; and removing unreacted epihalohydrin from the resin mixture to form the epoxy resin composition. In another embodiment, a process for separating a substrate from a substrate source is provided and includes: introducing an epihalohydrin with the substrate source comprising the substrate, the substrate comprising at least one hydroxyl group, and separating the epihalohydrin and the substrate from the substrate source.

21 Claims, 2 Drawing Sheets

(56) References Cited

U.S. PATENT DOCUMENTS

| | | | | |
|---|---|---|---|---|
| 2014/0194554 A1* | 7/2014 | Hefner, Jr. | C08G 59/145 | |
| | | | 523/400 | |
| 2016/0068498 A1 | 3/2016 | Haesakkers et al. | | |
| 2016/0244552 A1 | 8/2016 | Corley et al. | | |
| 2020/0331832 A1 | 10/2020 | Arita et al. | | |

OTHER PUBLICATIONS

International Search Report and Written Opinion dated Jul. 1, 2024 for Application No. PCT/US2024/021760.

Taiwan Office Action dated Jan. 14, 2025 for Application No. 113112286.

O. Gordobil et al., One-Step Lignin refining Process: The Influence of the Solvent Nature on the Properties and Quality of Fractions, Polymers 2022, 14(12), 2363, 20 pages.

O. Gordobil et al., One-Step Lignin refining Process: The Influence of the Solvent Nature on the Properties and Quality of Fractions, Polymers (2022), 14(12), 2363, Supporting information, 4 pages.

V. Ponnuchamy et al., Fractionation of lignin using organic solvents: A combined experimental and theoretical study, International Journal of Biological Macromolecules 168 (2021) 792-805.

T. Khan et al., Lignocellulose for Future Bioeconomy, Chapter 9—Lignin-Based Adhesive and Coatings, pp. 153-206., (2019).

X. Zhang et al., Critical role of solvent extraction sequence in the fractional separation of alkaline lignin, Fuel 322 (2022) 124268, 9 pages.

L. Carvalho Pereira Araújo et al., Kraft lignin fractionation by organic solvents: Correlation between molar mass and higher heating value, Bioresource Technology, vol. 314, 2020, 123757, 7 pages.

* cited by examiner

PROCESSES FOR FORMING EPOXY RESIN COMPOSITIONS AND SEPARATION PROCESSES

FIELD

Embodiments of the present disclosure generally relate to processes for forming epoxy resin compositions and processes for separating substrates from complex mixtures.

BACKGROUND

The synthesis of epoxy resins, such as liquid epoxy resin (LER) compositions and solid epoxy resin (SER) compositions, involves a reaction carried out in two steps to convert a hydroxyl-containing substrate (for example, a phenolic substrate) or an amine-containing substrate to a product mixture comprising a glycidated product using, for example, epichlorohydrin (ECH). The product mixture is discharged from the reactor and transferred to a separate reactor for work up. The work-up process is carried out on the product mixture to remove salt formed during glycidation, remove excess ECH, and to convert a halohydrin reaction product to the desired glycidation product. Problems arise when the conventional work-up process is applied to unconventional substrates, such as alcohols (for example phenols) of biological origin, alcohols present in an epoxy resin recycle stream, and alcohols present in a phenolic resin recycle stream. For example, when glycidation is performed on an unconventional substrate, the resulting product mixture is, for example, insoluble in solvents used for the work-up process. Further, the product mixture is too viscous to be discharged or removed from the glycidation reactor and transferred to the reactor for performing the work-up process. Even if the product mixture is not transferred to a different reactor, the halohydrin reaction product present in the product mixture cannot undergo conversion to the desired glycidyl ether as the halohydrin reaction product is not soluble in solvents used for the conversion.

In addition, the unconventional substrates often come from waste streams that are not purified or are crude raw materials. For example, alcohols of biological origin may come from a lignin waste stream and alcohols present in an epoxy resin or phenolic resin may come from recycled epoxy resins and phenolic resins, respectively. In each case, the hydroxyl-containing substrates to be converted to desired glycidyl ethers are present in complex compositions. Conventionally, the waste streams are purified by some form of fractionation or depolymerization, after which glycidation is attempted. Both fractionation and depolymerization utilize solvents that are not carried forward to downstream glycidation processes and instead are recycled or discarded. Beyond solvents, such additional steps can increase process complexity and cost, making use of waste streams for glycidation not commercially attractive.

Therefore, there is a need for new and improved processes for forming epoxy resin compositions. There is also a need for new and improved processes for separating substrates from raw materials and recycle streams.

SUMMARY

Embodiments of the present disclosure generally relate to processes for forming epoxy resin compositions. Unlike conventional technologies, embodiments described herein can be utilized to form epoxy resin compositions from, for example, bio-based substrates (alcohols of biological origin), as well as alcohols present in resin recycle streams (such as epoxy resin waste streams and phenolic resin waste streams), or combinations thereof.

Embodiments of the present disclosure also relate to processes for separating substrates, such as substrates used for glycidation reactions, from complex mixtures such as raw materials, waste streams, or recycle streams, among other complex mixtures. Unlike conventional technologies for separating glycidation substrates (alcohols) from complex mixtures, embodiments described herein enable reduced resin production costs, by, for example, using an epihalohydrin as a solvent for the extraction.

In an embodiment, a process for forming an epoxy resin composition is provided. The process includes reacting a mixture comprising a substrate comprising at least one hydroxyl group, an epihalohydrin, and a catalyst to form a first composition comprising a halohydrin reaction product. The process further includes introducing an alkaline reagent with the first composition to form a second composition comprising an epoxy resin product, a residual halohydrin reaction product, and a salt. The process further includes introducing a liquid epoxy resin with the second composition to form a liquid resin mixture; and removing unreacted epihalohydrin from the liquid resin mixture to form the epoxy resin composition.

In another embodiment, a process for making a liquid epoxy resin composition is provided. The process includes reacting a mixture comprising an alcohol of biological origin, an epihalohydrin, and a catalyst to form a first composition comprising a halohydrin reaction product. The process further includes introducing an alkaline reagent with the first composition to form a second composition comprising a glycidated product, residual halohydrin reaction product, and a salt; introducing a liquid epoxy resin with the second composition to form a liquid resin mixture; and removing unreacted epihalohydrin from the liquid resin mixture. The process further includes separating the salt from the liquid resin mixture. After the separating the salt from the liquid resin mixture, the process further includes forming the liquid epoxy resin composition by: converting at least a portion of the residual halohydrin reaction product in the liquid resin mixture to an epoxy resin; performing a liquid-liquid separation of the liquid resin mixture; or combinations thereof.

In another embodiment, a process for converting a substrate to a liquid epoxy resin composition is provided. The process includes reacting a mixture comprising the substrate, an epihalohydrin, and a catalyst to form a first composition comprising a halohydrin reaction product and a salt, the substrate comprising an alcohol of biological origin, an alcohol present in a resin waste stream, an alcohol present in a resin recycle stream, or combinations thereof. The process further includes introducing an alkaline reagent with the first composition to form a second composition comprising a glycidated product, residual halohydrin reaction product, and a salt; and introducing a liquid epoxy resin with the second composition to form a liquid resin mixture, the liquid epoxy resin having a viscosity that is about 15 Pa·s or less at 25° C. The process further includes removing unreacted epihalohydrin from the liquid resin mixture; and separating the salt from the liquid resin mixture to form the liquid epoxy resin composition.

In another embodiment, a process is provided. The process includes introducing an epihalohydrin with a substrate source comprising a substrate, the substrate comprising at least one hydroxyl group; and separating the epihalohydrin and the substrate from the substrate source.

In another embodiment, a process is provided. The process includes introducing an acid solution and an epihalohydrin with a substrate source comprising a substrate, the substrate comprising at least one hydroxyl group; and separating the epihalohydrin and the substrate from the substrate source.

In another embodiment, a process for making an epoxy resin composition is provided. The process includes introducing a first epihalohydrin with a substrate source, the substrate source comprising a substrate, the substrate comprising at least one hydroxyl group; separating at least a portion of the first epihalohydrin and the substrate from the substrate source; and converting the substrate to the epoxy resin composition.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

Figure 1:
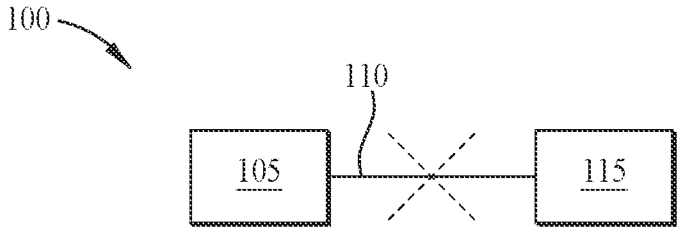
FIG. 1 is a flow diagram illustrating a conventional process for forming epoxy resin compositions.

Figures included herein illustrate various embodiments of the disclosure. It is contemplated that elements and features of one embodiment may be beneficially incorporated in other embodiments without further recitation.

DETAILED DESCRIPTION

Embodiments of the present disclosure generally relate to processes for forming epoxy resin compositions. Embodiments of the present disclosure also relate to processes for separating substrates from complex mixtures.

Unlike conventional technologies, embodiments described herein can be utilized to form epoxy resin compositions from, for example, bio-based substrates (alcohols of biological origin), as well as alcohols present in resin recycle streams (such as epoxy resin waste streams and phenolic resin waste streams), or combinations thereof. Such alcohols can include phenols and aliphatic alcohols, among others. Further, embodiments described herein can be used with existing production facilities without the need for retrofitting such production facilities. Embodiments of the present disclosure can enable simple and effective glycidation of unconventional substrates with superior work-up efficiencies. Further, embodiments described herein can reduce production costs of bio-based resin compositions and circumvent reactor downtime for cleaning.

Embodiments of the present disclosure also relate to processes for separating substrates, such as substrates used for glycidation reactions, from complex mixtures such as raw materials, waste streams, or recycle streams, among other complex mixtures. Unlike conventional technologies for separating glycidation substrates (alcohols) from complex mixtures, embodiments described herein enable reduced resin production costs, by, for example, using an epihalohydrin as a solvent.

The use of headings is for purposes of convenience only and does not limit the scope of the present disclosure. Embodiments described herein can be combined with other embodiments.

As used herein, a "composition" can include component(s) of the composition, reaction product(s) of two or more components of the composition, a remainder balance of remaining starting component(s), or combinations thereof. Compositions of the present disclosure can be prepared by any suitable mixing process.

As described above, conventional processes for forming epoxy resin compositions from unconventional substrates—such as alcohols of biological origin (for example, polyhydric phenols of biological origin), or alcohols present in recycle streams comprising epoxy resins or phenolic resins)—fail or are inefficient. Such failures and inefficiencies can be due to the high viscosity and insolubility of the product mixture formed from glycidation. For example, the work-up process to remove salt, excess ECH, and byproducts from the glycidation is conventionally performed using methyl isobutyl ketone (MIBK), toluene, xylene, dichloromethane, hexanes, or methyl ethyl ketone (MEK). Such solvents fail to solubilize the product mixture of the glycidation reaction when the glycidation reaction is performed on unconventional substrates such as alcohols, phenols, polyhydric alcohols, and polyhydric phenols of biological origin or present in recycle streams.

As used herein, a substrate comprising at least one alcohol (an alcohol of biological origin, an alcohol present in a waste stream, an alcohol present in a recycle stream, among others) is a reactant for a reaction.

As used herein, "phenolic substrate" and "polyhydric phenol" are used interchangeably such that recitation of one includes recitation of the other. For example, recitation of polyhydric phenols includes both "polyhydric phenol" and "phenolic substrate".

Alcohols of biological origin and alcohols present in recycle streams refer to compounds that have at least one hydroxyl (—OH) group present in the compound. The at least one hydroxyl group can be present as a phenolic hydroxyl, a hydroxyl group attached to a carbon that is non-aromatic (such as an alkyl hydroxyl), or combinations thereof. The alcohols of biological origin and alcohols present in recycle streams can include polyhydric alcohols (compounds containing more than one alcohol), polyhydric phenols (compounds containing more than one phenol), combinations thereof, among others.

FIG. 1 is a flow diagram illustrating a conventional process for forming an epoxy resin composition. The conventional process 100 includes a reaction sub-process 105 and a work-up sub-process 115 that occur in separate units. The reaction sub-process 105 and the work-up sub-process 115 can occur in the same unit. The reaction sub-process 105 is a glycidation reaction. The reaction sub-process 105 is coupled to the work-up sub-process 115 as represented by line 110. The reaction sub-process 105 includes reaction a substrate (such as a bisphenol) with an epihalohydrin in the presence of a catalyst to form a product mixture that includes a glycidated product. The reaction sub-process 105 includes a coupling reaction of the epihalohydrin with the bisphenol to form a halohydrin reaction product (an intermediate species). The reaction sub-process 105 also includes a ring-closure reaction of the halohydrin reaction product to form the glycidated product. Sometimes, a small proportion of halohydrin reaction product remains in the product mixture that includes glycidated product. This residual of halohydrin reaction product can be converted to the glycidated product during the work-up sub-process 115. Once the reaction is deemed complete in reaction sub-process 105, epihalohydrin is removed, and the product mixture is passed to work-up sub-process 115 via the line 110. The work-up sub-process 115 includes removing salt and brine by a phase separation using an organic solvent such as methyl isobutyl ketone (MIBK), toluene, xylene, dichloromethane, hexanes, or methyl ethyl ketone (MEK), among others. The organic phase having reaction products and intermediate species (for example, a halohydrin reaction product) is then subjected to another ring-closure reaction where the intermediate species can be transformed to desired glycidated product. Salt and brine can be removed and residual organic solvent and water can be removed to form the epoxy resin composition.

Problems arise (as indicated by the "dashed X" along line 110) when unconventional substrates (such as alcohols of biological origin, phenols of biological origin, alcohols present in recycle streams comprising epoxy resins or phenolic resins, phenols present in recycle streams comprising epoxy resins or phenolic resins, or combinations, among others) are used for the conventional process 100. For example, when certain unconventional substrates are submitted to the reaction sub-process, the product mixture exiting a line 110 is insoluble in organic solvents, is too viscous to be usable for further processing, or is too viscous to be removed from the coupling unit and fed to the work-up unit, among other problems. Overall, the conventional process 100 is not suitable for, at least, unconventional substrates.

Figure 2:
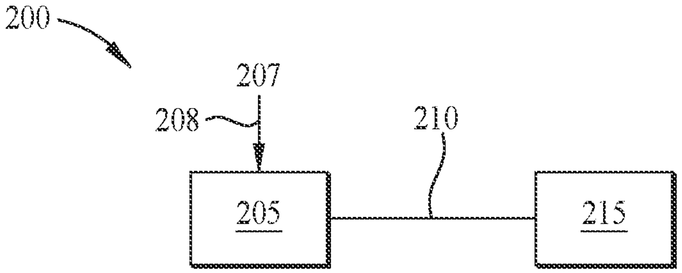
FIG. 2 is a flow diagram illustrating a process for forming an epoxy resin composition according to at least one embodiment of the present disclosure.

The inventors have found that addition of a liquid epoxy resin to the product mixture formed from glycidation facilitates the work-up process. FIG. 2 is a flow diagram illustrating a process 200 for forming epoxy resin compositions according to at least one embodiment of the present disclosure. Unlike conventional processes for forming epoxy resin compositions, the process 200 and embodiments of processes described herein can enable use of unconventional substrates (such as alcohols of biological origin, phenols of biological origin, alcohols present in recycle streams comprising epoxy resins or phenolic resins, phenols present in recycle streams comprising epoxy resins or phenolic resins, or combinations, among others). Conventional substrates (for example, non-biologically derived phenols or non-biologically derived alcohols) can also be used with processes described herein.

The process 200 includes a reaction sub-process 205 and a work-up sub-process 215. In some embodiments, the reaction sub-process 205 can be performed in a coupling unit or reactor, and the work-up sub-process 215 can be performed in a work-up unit or reactor. Here, line 210 represents, for example, feeding of the product mixture formed in the reaction sub-process 205 from a coupling unit to a work-up unit where the work-up sub-process 215 is performed. That is, the reaction sub-process 205 and the work-up sub-process 215 are coupled such that the individual units or reactors are coupled. Alternatively, line 210 can represent that the work-up sub-process 215 is to be performed and that the work-up sub-process 215 can be carried out in the same reactor as that reactor used for the reaction sub-process 205, or carried out in situ, or carried out continuously.

The reaction sub-process 205 includes coupling a substrate (such as a bisphenol, aliphatic alcohol, or combinations thereof) with an epihalohydrin in the presence of a catalyst to form a halohydrin reaction product (or halohydrin intermediate). The reaction sub-process 205 also includes ring closure of the halohydrin reaction product to a product mixture that includes a glycidated product by use of an alkaline reagent. In some embodiments, the catalyst and the alkaline reagent can be the same. In at least one embodiment, the catalyst and the alkaline reagent can be different. In some embodiments, an alkaline reagent can be utilized to perform both the coupling and the ring closure, for example, sodium hydroxide, among others. Operations of the reaction sub-process 205 and the work-up sub-process 215 can be similar to reaction sub-process 105 and work-up sub-process 115.

However, and unlike conventional processes, prior to feeding the product from the reaction sub-process 205 to the work-up sub-process 215, a liquid epoxy resin 207 is added to the product of the reaction sub-process by line 208. The liquid epoxy resin (LER) can prevent gelling or solidification of the product from the glycidation upon removal of residual epihalohydrin. The addition of the LER to the product mixture can help solubilize, and reduce the viscosity of, the product mixture. The addition of the LER to the product mixture can also aid in discharging the product mixture from the reactor and transfer of the product mixture to a separate reactor for the work-up process. Further, the addition of the LER to the product mixture can assist in the removal of salts and brine formed during the ring-closure, the removal of by-products formed from the reaction, the removal of unreacted epihalohydrin, or combinations thereof. In such a manner, embodiments described herein enable use of unconventional substrates to be utilized to form epoxy resin compositions.

Embodiments described herein generally relate to processes for forming epoxy resin compositions. The process generally includes reacting a mixture of a substrate (such as an alcohol-containing substrate, such as a bisphenol), an epihalohydrin, and a catalyst, under reaction conditions to form a mixture comprising a reaction product. The process can further include addition of an alkaline reagent to the mixture to form a product mixture. The product mixture can include, for example, a glycidated product (an epoxy resin), and optionally one or more optional components (for example, residual halohydrin reaction product, solvent, unreacted epihalohydrin, combinations thereof, among other components). Prior to concluding the reaction (by, for example, removing excess epihalohydrin), a liquid epoxy resin is added to the mixture. The liquid epoxy resin is introduced to the reaction product to, for example, prevent solidification of the reaction product from the glycidation reaction upon removal of the epihalohydrin. When desired, the reaction can be stopped by, for example, removal of the epihalohydrin, to form an epoxy resin composition. In some embodiments, the reaction product can then be subjected to a work-up process that can include purification operations (for example, epihalohydrin removal, solvent removal, salt removal), another glycidation reaction, among other operations to form the purified epoxy resin composition.

As further described below, conventional processes for forming epoxy resin compositions are unable to utilize diverse substrates for the glycidation reaction. For example, conventional processes cannot utilize biologically-derived materials such as lignin to form epoxy resin composition. One reason for this problem is that the produced reaction product from the glycidation reaction becomes gel-like or solidifies. As a gel or a solid, the epoxy resin composition cannot be submitted to work-up processes that typically occur in a separate reactor as the glycidation reaction. Even if the produced reaction product is not transferred to a different reactor, the halohydrin reaction product present in the reaction product cannot undergo conversion in the work-up phase to the desired glycidyl ether as the halohydrin reaction product is in an insoluble mixture. When conversion of the halohydrin reaction product is not performed during the work-up phase, but is performed in the reaction stage, gelling and solidification remains a problem as glycidated product forms. In addition, solidification and gelling is a problem for washing and extraction using solvent(s), water, and combinations thereof.

Figure 3:
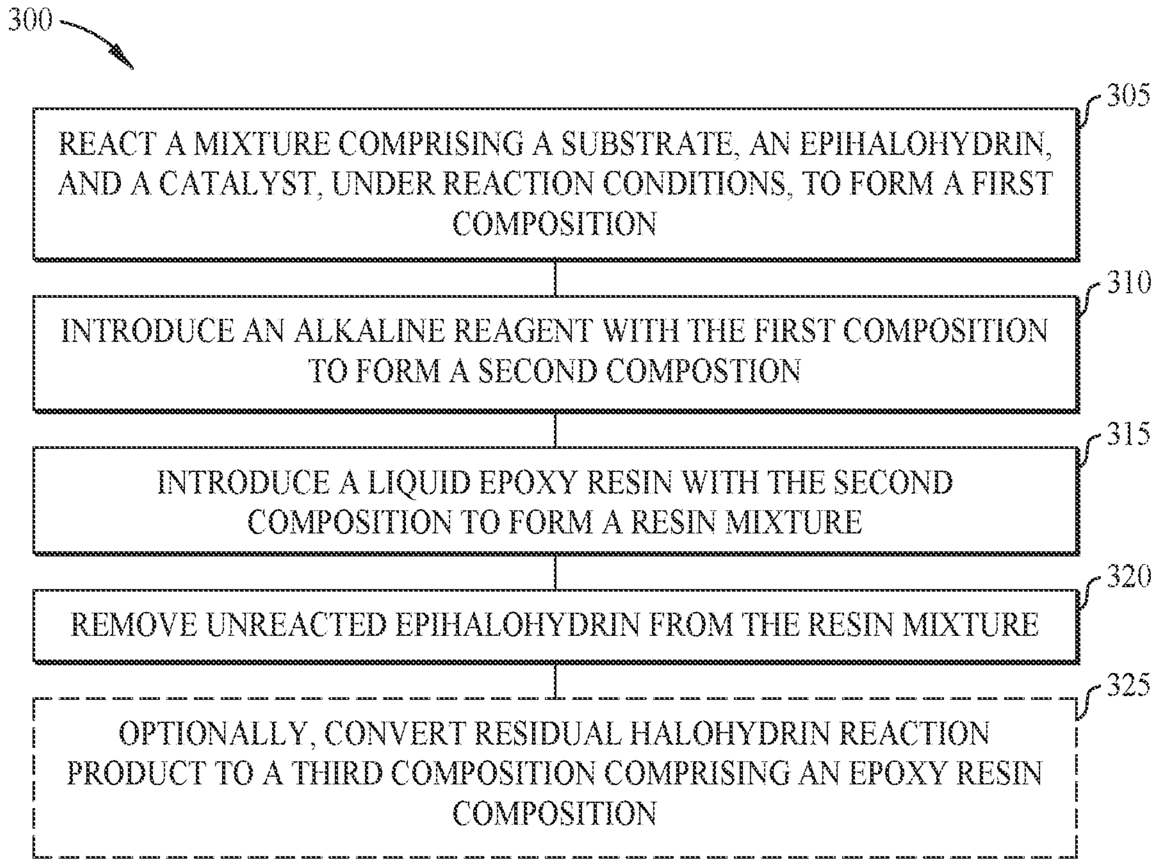
FIG. 3 is a flowchart showing selected operations of a process forming an epoxy resin composition according to at least one embodiment of the present disclosure.

FIG. 3 is a flowchart showing selected operations of a process 300 for forming an epoxy resin composition. FIG. 3 is a non-limiting example. The process 300 includes reacting a mixture comprising a substrate, an epihalohydrin, and a catalyst, under reaction conditions, to form a first composition at operation 305. The mixture can further include a solvent, among other components. The first composition formed by operation 305 can include a halohydrin reaction product (further described below), an epoxy resin (for example, a desired glycidated product), combinations thereof, among other components such as salts formed during the reaction.

Suitable substrates (compounds) for operation 305 can include alcohols of biological origin and alcohols present in recycle streams of resins. Substrates for operation 305 can interchangeably be referred to as glycidation substrates.

Suitable substrates can comprise at least one hydroxyl (—OH) group present in the substrate. The at least one hydroxyl group can be present as a phenolic hydroxyl, a hydroxyl group attached to a carbon that is non-aromatic (such as an alkyl hydroxyl or aliphatic hydroxyl), or combinations thereof. The alcohols of biological origin and alcohols present in recycle streams can include polyhydric alcohols (compounds containing more than one alcohol), polyhydric phenols (compounds containing more than one phenol such as bisphenols, trisphenols, tetraphenols, and so forth can be utilized), combinations thereof, among others. Substrates having an alcohol attached to an aromatic carbon and an alcohol attached to a non-aromatic carbon (for example, an alkyl hydroxyl) can be utilized. Additionally, substrates separated from the mixtures by embodiments described herein (for example, process 400 or process 500, described below) can be used as substrates for process 300.

Although embodiments described herein are discussed with reference to phenols, polyhydric phenols or phenol moieties for simplicity, it should be understood that any suitable substrate comprising at least one hydroxyl (—OH) group can be used.

Suitable alcohols useful with embodiments described herein (for example, operation 305) can include conventional alcohols (for example, polyhydric phenols synthesized and not of biological origin) used for glycidation as well as unconventional alcohols and unconventional polyhydric phenols. Unconventional alcohols and polyhydric phenols refers to alcohols and polyhydric phenols that are not conventionally used for forming epoxy resins, phenolic resins, among other resins, as well as alcohols and polyhydric phenols that are not conventionally used for glycidation reactions.

Unconventional alcohols and polyhydric phenols comprise, consist essentially of, or consist of alcohols and polyhydric phenols of biological origin (a living organism) and alcohols and polyhydric phenols that are derived from biological materials such as alcohols and polyhydric phenols present in biomass. In this context, biomass refers to biological material that can be converted to a resin. Illustrative, but non-limiting, examples of biomass include materials, by-products, and waste generated from, e.g., agricultural and forestry processes, such as agricultural matter and residues (e.g., wheat straw and corn), energy crops (e.g., wheatgrass and bamboo), forest residues (e.g., materials, by-products and waste from forest harvesting such as woodchips), plant- and algae-based matter and residues, and the like, and combinations thereof. In some embodiments, biomass includes wood, leaves, pulps, stalks, grass material, shrubs, branches, energy crops, vegetables, fruits, flowers, grains, herbaceous crops, bark, needles, logs, trees, nut shells, husks, and combinations thereof. Additionally, or alternatively, biomass includes municipal solid waste, by-products and waste from wood-processing, by-products and waste from papermaking or timber processes, by-products and waste from agricultural and forestry activities, rotation crops, lumber, wood chips, sawdust, straw, firewood, wood materials, paper, waste paper, yard waste, and the like. Accordingly, polyhydric phenols present in such materials (biomass) can be used with embodiments described herein.

Suitable alcohols can include alcohols (for example, polyhydric phenols and alkyl alcohols) present in technical lignin, Kraft lignin, and in organosolv lignin. Technical lignin refers to native lignin or proto-lignin derivative obtained as the result of the delignification process of lignocellulosic biomass. Kraft lignin refers to an industrial lignin obtained from Kraft pulp by the Kraft process for converting a bio-based substrate (for example, one of those above, such as wood) to pulp. Organosolv lignin refers to lignin obtained by organosolv, a pulping technique that uses an organic solvent to solubilize lignin and hemicellulose.

Unconventional alcohols (for example, polyhydric phenols and alkyl alcohols) comprise, consist essentially of, or consist of alcohols present in recycle streams or waste streams comprising epoxy resins, phenolic resins, or combinations thereof, among other resins. These waste streams and recycle streams can be those waste/recycle streams used or made during processing or manufacturing of resins.

In some embodiments, the unconventional alcohols can form part of a mixture or complex mixture of material. This mixture or complex mixture is referred to as a substrate source. As described below, and if desired, such substrate sources can be treated to extract or otherwise separate the desired unconventional alcohol (the substrate) to be used for glycidation from the substrate source. Non-limiting examples of processes for separating desired substrates from substrate sources are described below with respect to, for example, process 400 and process 500.

In some embodiments, suitable polyhydric phenols include mononuclear and polynuclear polyhydric phenols including those represented by formula (Ia), formula (Ib), formula (Ic), formula (Id), or combinations thereof:

$$(R)_2\text{-Ph-}(A)_n\text{-Ph-}(R)_2 \quad \text{(Ia);}$$

$$R\text{-Ph-}[A\text{-Ph}]_m\text{—}R \quad \text{(Ib);}$$

$$R\text{-Ph-}A^1\text{—}(\text{Ph-}R)_2 \quad \text{(Ic); or}$$

(Id)

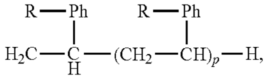

wherein, for formulas (Ia)-(Id):

Ph is a phenol group (an aromatic group with a hydroxyl functional group);

each A group is independently an unsubstituted hydrocarbyl, a substituted hydrocarbyl, or a functional group comprising at least one element from Group 13-17 of the periodic table of the elements, and each A group is independently divalent, trivalent, or tetravalent;

each $A^1$ group is an unsubstituted hydrocarbyl, a substituted hydrocarbyl, or a functional group comprising at least one element from Group 13-17 of the periodic table of the elements, and each $A^1$ group is independently divalent, trivalent, or tetravalent;

each R group is independently hydrogen, an unsubstituted hydrocarbyl, a substituted hydrocarbyl, or a functional group comprising at least one element from Group 13-17 of the periodic table of the elements, and each R group within the same polyhydric phenol can be the same or different;

m is from 1 to 6, such as from 1 to 3 or 1, 2, 3, 4, 5, or 6;

n is 0 or 1; and p is from 1 to 100, such as from 1 to 20, such as from 1 to 10, such as from 1 to 5, such as 1, 2, 3, 4, or 5.

When an A group, an $A^1$ group, or an R group is a functional group comprising at least one element from Group 13-17, the A group, the $A^1$ group, or the R group can be halogen (F, Cl, Br, or I), O, N, Se, Te, P, As, Sb, S, B, Si, Ge, Sn, Pb, and the like, such as C(O)R*, C(C)NR*$_2$, C(O)OR*, NR*$_2$, OR*, SeR*, TeR*, PR*$_2$, AsR*$_2$, SbR*$_2$, SR*, $SO_x$ (where x=2 or 3), BR*$_2$, SiR*$_3$, GeR*$_3$, SnR*$_3$, PbR*$_3$, and the like, where R* is, independently, hydrogen or unsubstituted hydrocarbyl, or where at least one heteroatom has been inserted within the unsubstituted hydrocarbyl.

Each of A, $A^1$, and R of formulas (Ia)-(Id) can have, independently, any suitable number of carbon atoms such as from 1 to 20 carbon atoms, such as from about 1 to about 12 carbon atoms, such as from 1 to 10 carbon atoms, such as from 1 to 5 carbon atoms, such as from 1 to 4 carbon atoms. In some embodiments, the number of carbon atoms in A, $A^1$, and R of formulas (Ia)-(Id) can be, independently, 1, 2, 3, 4, 5, 6, 7, 8, 9, 10, 11, 12, 13, 14, 15, 16, 17, 18, 19, or 20. Each of the foregoing numbers can be preceded by the word "about," "at least about," "less than about," or "more than about," and any of the foregoing numbers can be used singly to describe an open-ended range or in combination to describe a close-ended range. Each of A, $A^1$, and R of formulas (Ia)-(Id) can be, independently, linear or branched, saturated or unsaturated, cyclic or acyclic, aromatic or not aromatic. Regarding saturation, each of A, $A^1$, and R of formulas (Ia)-(Id) can be, independently, fully saturated, partially unsaturated, or fully unsaturated.

In some examples, each of A, $A^1$, and R of formulas (Ia)-(Id) can be an unsubstituted hydrocarbyl. An "unsubstituted hydrocarbyl" refers to a group that consists of hydrogen and carbon atoms only. Non-limiting examples of unsubstituted hydrocarbyl include an alkyl group having from 1 to 20 carbon atoms such as methyl, ethyl, n-propyl, isopropyl, n-butyl, iso-butyl, sec-butyl, and tert-butyl, pentyl, hexyl, heptyl, octyl, ethyl-2-hexyl, isooctyl, nonyl, n-decyl, isodecyl, or isomers thereof; a cycloaliphatic group having from 3 to 20 carbon atoms such as, for example, cyclopentyl or cyclohexyl; an aromatic group having from 6 to 20 carbon atoms such as, for example, phenyl or naphthyl; or any combination thereof.

In some embodiments, each of A, $A^1$, and R of formulas (Ia)-(Id) can be a substituted hydrocarbyl. A "substituted hydrocarbyl" refers to an unsubstituted hydrocarbyl in which at least one hydrogen of the unsubstituted hydrocarbyl has been substituted with at least one heteroatom or heteroatom-containing group, such as one or more elements from Group 13-17 of the periodic table of the elements, such as halogen (F, Cl, Br, or I), O, N, Se, Te, P, As, Sb, S, B, Si, Ge, Sn, Pb, and the like, such as C(O)R*, C(C)NR*$_2$, C(O)OR*, NR*$_2$, OR*, SeR*, TeR*, PR*$_2$, AsR*$_2$, SbR*$_2$, SR*, $SO_x$ (where x=2 or 3), BR*$_2$, SiR*$_3$, GeR*$_3$, SnR*$_3$, PbR*$_3$, and the like, where R* is, independently, hydrogen or unsubstituted hydrocarbyl, or where at least one heteroatom has been inserted within the unsubstituted hydrocarbyl.

In at least one embodiment, each A group of formulas (Ia)-(Id) is independently a divalent hydrocarbyl group having from 1 to 12 carbon atoms, —O—, —S—, —S—S—

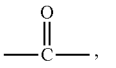, 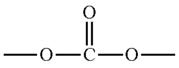, 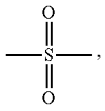, or 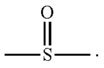.

In some embodiments of formulas (Ia)-(Id), each A is independently a divalent group, $A^1$ is a trivalent group, or combinations thereof.

In some embodiments, each R group of formulas (Ia)-(Id) is independently hydrogen, an unsubstituted hydrocarbyl having from 1 to 10 carbon atoms, a halogen (such as Cl or Br), a hydroxyl (—OH), or a substituted hydrocarbyl having from 1 to 10 carbon atoms. For example, the substituted hydrocarbyl can be —OR*, where the oxygen atom is connected to the ring and where R* can include 1 to 10 carbon atoms, such as 1 to 5 carbon atoms, such as 2 to 4 carbon atoms. As another example, the substituted hydrocarbyl can be a hydrocarbon chain bearing an OH or OR*, or the substituted hydrocarbyl can be an aromatic unit bearing an OH or OR*.

In some embodiments, the polyhydric phenol is represented by formula (II):

(II)

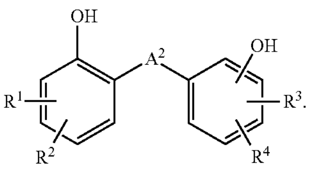

In formula (II), $A^2$ is a divalent group, a trivalent group, or a tetravalent group such as those described above for A in formulas (Ia)-(Id). In formula (II), each of $R^1$, $R^2$, $R^3$, and $R^4$ can be an R group described above for R in formulas (Ia)-(Id), such as hydrogen, an unsubstituted hydrocarbyl, a substituted hydrocarbyl, or a functional group comprising at least one element from Group 13-17 of the periodic table of the elements. Each of $R^1$, $R^2$, $R^3$, and $R^4$ in formula (II) can be the same or different.

As shown in formula (II), each of $R^1$ and $R^2$ is independently located on the aromatic ring at a position that is ortho, meta, para to the hydroxyl group. Each of $R^3$, $R^4$, and the hydroxyl (—OH) group is independently located on the aromatic ring at a position that is ortho, meta, para to $A^2$. In some embodiments, each of $R^1$, $R^2$, $R^3$, and $R^4$ in formula (II) can be independently hydrogen, unsubstituted hydrocarbyl having 1 to 20 carbon atoms (such as from 1 to 12, such as from 1 to 10, such as from 2 to 6), substituted hydrocarbyl, having 1 to 20 carbon atoms (such as from 1 to 12, such as from 1 to 10, such as from 2 to 6). In at least one embodiment, each of $R^1$, $R^2$, $R^3$, and $R^4$ in formula (II) can be independently-OH group, an alkyl group bearing a —OH group, an —OR* group, an alkyl group bearing an —OR* group, an aromatic group having from 6 to 20 carbon atoms (such as phenyl, naphthyl, among others), or an aromatic group having from 6 to 20 carbon atoms and bearing an —OR* group. For the —OR* group, the oxygen atom is connected to the aromatic ring and R* can include 1 to 10 carbon atoms, such as 1 to 5 carbon atoms, such as 2 to 4 carbon atoms. For example, —OR* can be alkyloxy such as methoxy, ethoxy, propoxy, butoxy, and isomers thereof.

In some embodiments, each of $R^1$, $R^2$, $R^3$, and $R^4$ in formula (II) is independently a group that is non-reactive with an epoxide-bearing reactant. For example, and in at least one embodiment, each of $R^1$, $R^2$, $R^3$, and $R^4$ in formula (II) is independently —(C1-C5)alkyl or —O(C1-C5)alkyl.

In at least one embodiment, the phenol of formula (I) is a bisphenol. In formula (II), and in some embodiments, at least one of $R^1$ or $R^2$ is located at an ortho position on the aromatic ring relative to the hydroxyl group. In some embodiments, at least one of $R^3$ or $R^4$ is located on the aromatic ring at a position that is meta to $A^2$. In some embodiments, the hydroxyl group of the aromatic ring (on the right side of formula (II)) is located on the on the aromatic ring at a position that is para to $A^2$.

Illustrative, but non-limiting examples of polyhydric phenols of formula (II) include tetramethyl bisphenol F (TMBPF; CAS Number: 5384-21-4; also known as 4,4'-methylenebis(2,6-dimethylphenol)) (IIa); 4,4'-methylenebis (2,6-diethylphenol) (CAS Number: 73576-37-1, (IIb)); 4,4'-methylenebis(2,6-diisopropylphenol) (CAS Number: 24742-46-9, (IIc)); 4,4'-methylenebis(2,6-di-tert-butylphenol) (CAS Number: 118-82-1, (IId)); 4,4'-methylenebis(2,6-dimethoxyphenol) (CAS Number: 15640-40-1, (IIe)); bisphenol A (TMBPA; CAS Number: 5613-46-7) (IIf); or combinations thereof:

(IIa)

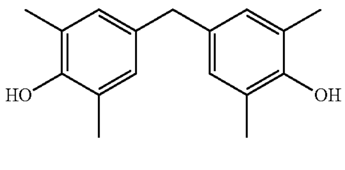

(IIb)

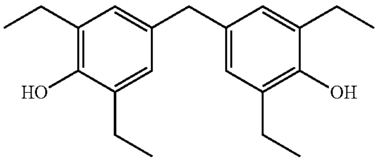

-continued (IIc)

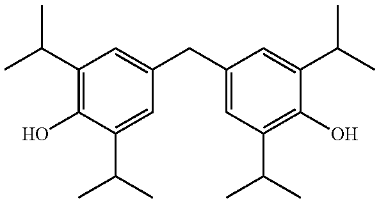

(IId)

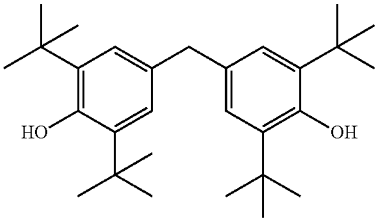

(IIe)

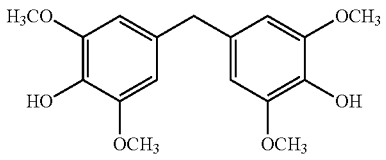

(IIf)

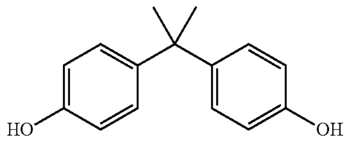

The polyhydric phenols described above can have a biological origin (for example, sourced from biomass, or sourced from processes that convert biomass to products, such as technical lignin, Kraft lignin or organosolv lignin), or the polyhydric phenols can be synthesized (that is from non-biological origin).

As described above, the substrate for glycidation (for example, operation 305) can include components of (or be sourced from) a recycle stream, the recycle stream comprising an epoxy resin, a phenolic resin, or combinations thereof. Illustrative, but non-limiting, examples of such substrates sourced from recycle streams include novolac resins, epoxy novolacs, phenolic oligomers from pyrolyzed composites based on bisphenol A-liquid epoxy resin, and phenolic oligomers from solvolyzed composites based on bisphenol A-liquid epoxy resin.

Substrates useful for the glycidation reaction (for example, operation 305) can also include a resin represented by formula (III) or derivatives thereof:

(III)

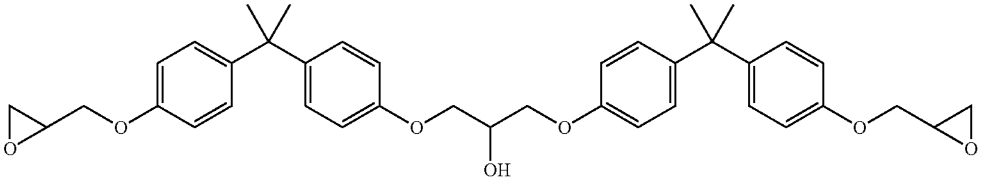

In formula (III), x can be from 1 to 20, such as from 1 to 10, such as from 4 to 8. In some embodiments, x of formula (III) can be 1, 2, 3, 4, 5, 6, 7, 8, 9, 10, 11, 12, 13, 14, 15, 16, 17, 18, 19, or 20. Each of the foregoing numbers can be preceded by the word "about," "at least about," "less than about," or "more than about," and any of the foregoing numbers can be used singly to describe an open-ended range or in combination to describe a close-ended range.

The resin represented by formula (III) is an example of a compound having a hydroxyl group present on a non-aromatic carbon (a substrate having an alkyl hydroxyl or aliphatic hydroxyl).

Suitable substrates for operation 305 can include any of the aforementioned materials, combinations of the aforementioned materials, in any proportion.

Suitable epihalohydrins for operation 305 include those represented by formula (IV):

(IV)

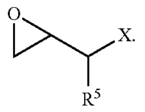

In formula (IV), $R^5$ is a hydrogen, an unsubstituted hydrocarbyl, or a substituted hydrocarbyl. The $R^5$ group of epihalohydrin shown in formula (IV) can include from 1 to 20 carbon atoms, such as from 1 to 10 carbon atoms, such as from 1 to 4 carbon atoms. The X group in formula (IV) is a halogen such as fluorine, chlorine, bromine, or iodine, such as chlorine or bromine. In some embodiments, the epihalohydrin comprises epichlorohydrin (X=Cl and $R^5$=H in formula (IV); CAS No. 106-89-8), epibromohydrin (X=Br and $R^5$=H in formula (IV); CAS No. 3132-64-7), or combinations thereof.

A solvent can be used during operation 305. The solvent for operation 305 is typically an organic solvent. Organic solvents for operation 305 can include alcohols, ketones, aromatic hydrocarbons, and halogenated aliphatic compounds such as, for example, isopropanol, ethanol, methanol, methyl isobutyl ketone, methyl ethyl ketone, toluene, xylene, methylene chloride, ethylene dichloride, mixtures thereof, among others. Combinations of solvents can be used. In at least one embodiment, an epihalohydrin can be used as a solvent. For example, epichlorohydrin can be used as both a reactant and a solvent.

As described above, the glycidated product (ring-closed epoxide product) can be formed from a substrate (such as a bisphenol, aliphatic alcohol, or combinations thereof) and an epihalohydrin reactant using an alkaline reagent, or an alkaline reagent and a catalyst.

Alkaline reagents can enable both coupling of the substrate with the epihalohydrin to form the halohydrin reaction product (or halohydrin intermediate) and ring closure of the halohydrin reaction product to the glycidated product. Catalysts, on the other hand, are selected to perform at least the coupling.

For example, ammonium and phosphonium salts can perform the coupling but are not alkaline enough to perform the ring closing reaction to the epoxide. In contrast, alkaline reagents such as sodium hydroxide can act both as the catalyst for the coupling and as the reagent for ring closure.

Process 300 further includes introducing an alkaline reagent with the first composition to form a second composition at operation 310. In some embodiments, operation 305 can be optional, for example, when the catalyst is also the alkaline reagent. When the catalyst is also the alkaline reagent, the alkaline reagent can act as both a catalyst in the start of the reaction (forming mainly the first composition comprising the halohydrin reaction product) and then in the later stage of the reaction (forming mainly the second composition comprising the ring closed glycidated product).

Operation 310 can performed under the same or similar conditions as described for operation 305. The second composition can include a product mixture that comprises, consists essentially of, or consists of an epoxy resin (the desired epoxy product), residual halohydrin reaction product, combinations thereof, among other components such as salts formed during the reaction.

Suitable catalysts useful for operation 305 can comprise, consist essentially of, or consist of alkali metal hydroxides, alkali earth metal hydroxides, ammonium salts, phosphonium salts, sulfonium salts, lithium salts, or combinations thereof. Non-limiting examples of alkali metal hydroxides can include, but are not limited to, sodium hydroxide, potassium hydroxide, lithium hydroxide, or combinations thereof, among others. Illustrative, but non-limiting, examples of alkali earth metal hydroxides include calcium hydroxide, magnesium hydroxide, combinations thereof, among others. Suitable ammonium salts include tetramethyl ammonium chloride, tetrabutyl ammonium chloride, tetrabutyl ammonium bromide, benzyl trimethyl ammonium chloride, benzyl triethyl ammonium chloride, tetraethyl ammonium chloride, tetraethanol ammonium chloride, tetraethanol ammonium hydroxide, or combinations thereof, among others. Suitable phosphonium salts include ethyl triphenyl phosphonium iodide, ethyl triphenyl phosphonium bicarbonate, benzyl triphenyl phosphonium chloride, tetrabutyl phosphonium chloride and the like. Suitable sulfonium salts include thiourea catalysts such as tetramethyl thiourea, N,N'-diphenyl thiourea. Mixtures of catalysts can be used with embodiments herein. In at least one embodiment, the catalyst comprises, consists essentially of, or consists of sodium hydroxide, potassium hydroxide, calcium hydroxide, tetramethyl ammonium chloride (TMAC), tetrabutyl ammonium chloride (TBAC), tetrabutyl ammonium bromide (TBAB), or combinations thereof.

Suitable alkaline reagents can include, but are not limited to, alkali metal hydroxides, alkali earth metal hydroxides, or combinations thereof, such as sodium hydroxide (NaOH), potassium hydroxide (KOH), lithium hydroxide (LiOH), calcium hydroxide ($Ca(OH)_2$), magnesium hydroxide ($Mg(OH)_2$), or combinations thereof, such as NaOH, KOH, ($Ca(OH)_2$), or combinations thereof. Mixtures of alkaline reagents can be used with embodiments herein.

The epihalohydrin and the substrate can be provided at a molar ratio of epoxy group of the epihalohydrin to hydroxyl group of the substrate (aromatic hydroxyl, alkyl hydroxyl) that is from about 1:1 to about 50:1, such as from about 1.1 to about 35:1, such as from about 1.2:1 to about 20:1, such as from about 1.5:1 to about 10:1, though other amounts are contemplated. Any of the foregoing numbers can be used singly to describe an open-ended range or in combination to describe a close-ended range.

In some embodiments, the epihalohydrin and the substrate can be provided via a mass ratio such that there is an excess of epihalohydrin to substrate (greater than 1:1).

A weight ratio of solvent (for example, toluene or epihalohydrin) to substrate for operation 305 can be from about 1:1 to about 50:1, such as from about 2:1 to about 20:1, such as from about 5:1 to about 12:1, though other amounts are contemplated. Any of the foregoing numbers can be used singly to describe an open-ended range or in combination to describe a close-ended range.

The amount of catalyst used for operation 305 can be any quantity that will suitably catalyze the reaction between the polyhydric phenol and the epihalohydrin. The catalyst and the substrate can be provided at a molar ratio of catalyst to hydroxyl group of the substrate (for example, aromatic hydroxyl, alkyl hydroxyl) that is from about 0.01:1 to about 0.5:1, such as from about 0.05:1 to about 0.2:1, such as from about 0.1:1 to about 0.15:1, though other amounts are contemplated. Any of the foregoing numbers can be used singly to describe an open-ended range or in combination to describe a close-ended range.

The amount alkaline reagent used for the ring closing reaction in operation 310 is largely governed by the amount of epihalohydrin that reacts. For example, in glycidating a polyhydric phenol with an excess of more than two equivalents of epihalohydrin per hydroxyl group of the substrate (aromatic hydroxyl, alkyl hydroxyl), a molar excess of the catalyst per hydroxyl equivalent of the substrate is used, such as from about 1.2:1 to about 5:1, such as from about 1.5:1 to about 3.5:1, such as from about 2:1 to about 3:1, though other amounts are contemplated. Any of the foregoing numbers can be used singly to describe an open-ended range or in combination to describe a close-ended range.

In some embodiments, each of the catalyst (in operation 305), alkaline reagent (in operation 310), or combinations thereof, can independently be added to the substrate, epihalohydrin, and solvent as a solid or as a solution. When the catalyst or the alkaline reagent is brought together with the other reactants as a solution, the solution (catalyst or alkaline reagent in solvent) can include about 15% to about 65% by weight of catalyst or alkaline reagent, such as from about 20% to about 55% by weight of catalyst or alkaline reagent, such as from about 30% to about 45% by weight of catalyst or alkaline reagent, though other amounts are contemplated.

The reaction conditions of operation 310 can include a dosing time (or injection time), a post-dosing time (or a post-injection time) and a total reaction time. The dosing time is the period over which the alkaline reagent is added to the substrate, epihalohydrin, and solvent. The dosing time of operation 310 can be from about 10 minutes to about 8 hours, such as from about 40 minutes to about 6 hours, such as from about 1 hour to about 2 hours, though other periods are contemplated. Any of the foregoing numbers can be used singly to describe an open-ended range or in combination to describe a close-ended range.

The post-dosing time of operation 310 is the period after all of the alkaline reagent is dosed during operation 310 to the conclusion of the reaction of operation 310. The conclusion of the reaction can be based on the time point at which a certain percent conversion of the substrate has occurred. For example, the post-dosing time of operation 310 can be the amount of time between the conclusion of the dosing time and the point at which about 90% or more conversion of the halohydrin reaction product (or halohydrin intermediate species) to the ring closed product has occurred, such as about 91% or more conversion, such as about 92% or more conversion, such as about 93% or more conversion, such as about 94% or more conversion, such as about 95% or more conversion, such as about 96% or more conversion, such as about 97% or more conversion, such as about 98% or more conversion, such as about 99% or more conversion, such as about 99.9% or more conversion, such as about 100% conversion, though other amounts of conversion are contemplated. Any of the foregoing numbers can be used singly to describe an open-ended range or in combination to describe a close-ended range.

In some non-limiting examples, the post-dosing time of operation 310 can be from about 20 minutes to about 5 hours, such as from about 1 hour to about 3 hours, such as from about 1.5 hours to about 2 hours, though other periods are contemplated. Any of the foregoing numbers can be used singly to describe an open-ended range or in combination to describe a close-ended range.

The total reaction time of operation 310 is the sum of the dosing time and the post-dosing time. The total reaction time of operation 310 can be from about 0.5 hours to about 13 hours, such as from about 0.5 hours to about 9 hours, such as from about 1 hour to about 6 hours, such as from about 2 hours to about 4.5 hours, though other periods are contemplated. Any of the foregoing numbers can be used singly to describe an open-ended range or in combination to describe a close-ended range.

The reaction time of operation 305 can be from about 0.5 hours to about 13 hours, such as from about 0.5 hours to about 9 hours, such as from about 1 hour to about 6 hours, such as from about 2 hours to about 4.5 hours, though other periods are contemplated. Any of the foregoing numbers can be used singly to describe an open-ended range or in combination to describe a close-ended range.

The reaction conditions of operation 305, operation 310, or both, can include a reactor temperature that is from about 20° C. to about 100° C., such as from about 35° C. to about 95° C., such as from about 50° C. to about 90° C., though other temperatures are contemplated. Any of the foregoing numbers can be used singly to describe an open-ended range or in combination to describe a close-ended range. Reactor temperature is the temperature monitored by a temperature probe.

The reaction conditions of operation 305, operation 310, or both, can also include a reactor pressure as measured in units of absolute pressure. The reactor pressure can be from about 100 mbara (about 10 kPa (absolute)) to about 1,500 mbara ((about 150 kPa (absolute)), such as from about 150 mbara ((about 15 kPa (absolute)) to about 1,000 mbara ((about 100 kPa (absolute)), such as from about 200 mbara ((about 20 kPa (absolute)) to about 400 mbara ((about 40 kPa (absolute)), though other pressures are contemplated. Any of the foregoing numbers can be used singly to describe an open-ended range or in combination to describe a close-ended range.

The reaction conditions of operation 305, of operation 310, or both, can include stirring, mixing, agitation, or combinations thereof. The apparatus used to perform stirring, mixing or agitation can include a batch reaction vessel, a semi-batch reaction vessel, a continuous static mixer, or other suitable apparatus. Mechanical agitation or jet mixing can be used. In some embodiments, water and epichlorohydrin can be removed (for example, continuously or periodically) as a vapor from the reacting mixture by, for example, distillation during at least a portion of operation 305. The distillation can be an azeotropic distillation. The epihalohydrin can be returned or recycled to the reacting mixture.

The reaction conditions of operation 305, of operation 310, or both, can optionally include utilizing a non-reactive gas, such as nitrogen, argon, or combinations thereof. For example, the mixture comprising the substrate, epihalohydrin, solvent, and catalyst can be used with these or other non-reactive gases to degas various components or otherwise remove oxygen from the mixture.

As described herein, the first composition formed from operation 305, the second composition from operation 310, or both can include a glycidated product (an epoxy resin), for example, a product where a hydroxyl of the substrate has been converted to a glycidyl ether. Optionally, the first composition, the second composition, or both can include one or more optional components. The one or more optional components can include an intermediate species (for example, a halohydrin reaction product), salt, brine, solvent, unreacted starting materials (epihalohydrin, substrate, catalyst, or mixtures thereof), combinations thereof, among other components. As a non-limiting example, and as shown in Scheme 1, a glycidyl ether having formula (V-1), a halohydrin reaction product (or halohydrin intermediate species) having formula (V-2), or combinations thereof can form from the reaction of a polyhydric phenol (as an example alcohol) and an epihalohydrin.

Scheme 1

(V-I)

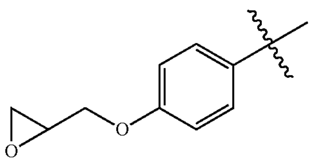

(V-2)

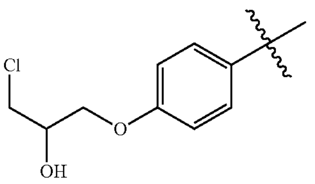

In formula (V-1) and formula (V-2), the wavy bond represents a connection to the other portion of the polyhydric phenol.

Process 300 further includes introducing a liquid epoxy resin (LER) with the second composition to form a resin mixture at operation 315. The resin mixture formed at operation 315 can be a liquid resin mixture. As described above, use of the LER can prevent gelling or solidification of the second composition (for example, the product of the reaction sub-process 205) upon removal of the epihalohydrin. The addition of the LER helps solubilize, and reduce the viscosity of, the second composition. The addition of the LER to the product mixture can also aid in discharging the second composition from the unit or reactor used for the reaction sub-process 205 and transfer of the second composition to the separate unit or reactor where the work-up sub-process 215 occurs. Further, the addition of the LER to the product mixture can assist in the removal of salts and brine formed during the glycidation, the removal of by-products formed from the glycidation, the removal of unreacted epihalohydrin, or combinations thereof, among other materials. In such a manner, embodiments described herein enable use of unconventional substrates to be utilized to form epoxy resin compositions.

Addition of an LER during the glycidation is not obvious for at least the reason that the LER would be exposed to reaction conditions, alkaline conditions, hydrolytic conditions, which one would normally want to prevent. However, adding an LER during glycidation enables the realization of various benefits as described herein.

Epoxy resins that can be used as an LER for operation 315 include polymers based on an epoxide compound which can be a reaction product of a polyfunctional hydroxyl compound with an epihalohydrin (for example, epichlorohydrin, epibromohydrin, among others). The crosslinking of the polymer matrix takes place by polyaddition over the epoxide groups.

Epoxy resins useful as an LER for operation 315 can include epoxy resins based on bisphenol A, bisphenol F, advancement resins produced therefrom; epoxy resins based on tetraglycidyl-methylenedianiline (TGMDA); epoxy resins based on epoxidized halogenated bisphenols; epoxy resins based on epoxidized novolaks; epoxy resins based on epoxidized ortho- or para-aminophenols; epoxy resins based on epoxidized polyaddition products of dicyclopentadiene and phenol; epoxy resins based on flourenone bisphenols; or combinations thereof. In some embodiments, an epoxy resin useful as an LER for operation 315 is derived from bisphenol A, bisphenol F, tetraglycidyl-methylenedianiline, a halogenated bisphenol, a novolak, an ortho-aminophenol, a para-aminophenol, a polyaddition product of dicyclopentadiene and phenol, a flourenone bisphenol, or combinations thereof. Such materials can be reacted with an epoxide-containing reactant (such as an epihalohydrin) to form an epoxide or epoxy resins. For example, the epoxy resin can include epoxidized phenol novolaks (condensation product of phenol and, for example, formaldehyde, glyoxal, or combinations thereof), epoxidized cresol novolaks, epoxy resins based on bisphenol A (for example, a product of bisphenol A and tetraglycidylmethylenedianiline), epoxidized halogenated bisphenols (for example, epoxy resins based on tetrabromobisphenol A), epoxy resins based on bisphenol F, epoxidized novolak, or combinations thereof.

Other epoxy resins useful as an LER for operation 315 can include epoxides of aliphatic mono-alcohols, epoxides of aliphatic bis-alcohols. Such aliphatic alcohols have low viscosity. The aliphatic mono- or bis-alcohols can contain cyclic elements, linear elements of combinations thereof. Illustrative, but non-limiting, examples can include glycidyl ethers of 1,4-butanediol, glycidyl ethers 1,6-hexanediol, monoglycidyl ethers of C6 to C14 aliphatic chains, among others.

In some embodiments, epoxy resins suitable as an LER for operation 315 include liquid epoxy resins having a low viscosity. "Low viscosity" in the context of an epoxy resin means that the epoxy resin has a viscosity that is less than about 15 Pas at 25° C. (ASTM D-445).

The epoxy resin used as an LER can have a viscosity that is from about 0.002 Pa·s to about 15 Pa·s, such as from about 0.01 Pas to about 6.5 Pas, such as from about 0.02 Pa·s to about 3 Pa·s, though other viscosities are contemplated. The viscosity of the epoxy resin used as an LER is determined at 25° C. using ASTM D-445.

Suitable liquid epoxy resins having a low viscosity include aromatic epoxy resins and aliphatic epoxy resins. Illustrative, but non-limiting, examples of such aromatic epoxy resins can include, but are not limited to, Epikote 828 (a difunctional bisphenol-A-diglycidyl-ether commercially available from Westlake Epoxy), Epikote 828LVEL (a difunctional bisphenol-A-diglycidyl-ether commercially available from Westlake Epoxy), Epikote 827 (a difunctional bisphenol-A-diglycidyl-ether commercially available from Westlake Epoxy), Epikote 862 (a difunctional bisphenol-F-diglycidyl-ether commercially available from Westlake Epoxy), Epikote 496 (a tetra-glycidyl-methylene-dianiline commercially available from Westlake Epoxy), Epikote 1031 (an epoxidized tetra-phenylethane commercially available from Westlake Epoxy), EPON 826 (a difunctional bisphenol-A-diglycidyl-ether commercially available from Westlake Epoxy), EPON 828 (a difunctional bisphenol-A-diglycidyl-ether commercially available from Westlake Epoxy), D.E.R. 330 (a liquid epoxy resin reaction product of epichlorohydrin and bisphenol A commercially available from Olin).

Illustrative, but non-limiting, examples of aliphatic epoxy resins having a low viscosity can include, but are not limited to, Heloxy Z8 (an aliphatic monoglycidyl ether of C12/C14-fatty alcohol commercially available from Westlake Epoxy), Heloxy BD (a diglycidyl ether of 1,4-butanediol commercially available from Westlake Epoxy), and Heloxy HD (a diglycidyl ether of 1,4-hexanediol commercially available from Westlake Epoxy).

The type of LER added can be matched to the application for which the final epoxy resin composition will be used. In some embodiments, the selection of LER can be based on its ability to form a homogeneous mixture with the second composition, its ability to mix with the second composition, among other factors, or combinations thereof.

In some embodiments, an amount of LER added to the second composition is based on the amount of epoxy group content formed from reaction sub-process 205 (for example, epoxy group content of the second composition). Here, a weight ratio of LER:Epoxy in the second composition can be from about 0.02:1 to about 1.5:1, such as from about 0.05:1 to about 1.25:1, such as from about 0.25:1 to about 1:1, such as from about 0.5:1 to about 1:1, though other amounts are contemplated. Any of the foregoing numbers can be used singly to describe an open-ended range or in combination to describe a close-ended range.

At this stage, the resin mixture comprises, consists essentially of, or consists of a LER and a glycidyl ether (as an example desired product, for example, a glycidyl ether of formula (V-1)). The resin mixture can also include one or more optional components such as a halohydrin reaction product (for example, a halohydrin reaction product of formula (V-2)), unreacted epihalohydrin, solvent, water, salt, combinations thereof, among other components.

Process 300 can further include removing unreacted epihalohydrin from the resin mixture (for example, the liquid resin mixture) at operation 320. Removal of unreacted epihalohydrin can be performed by, for example, evaporation or distillation (under suitable conditions), among other methods. Here, for example, and depending on the epihalohydrin, a distillation temperature can be from about 70° C. to about 150° C., such as from about 90° C. to about 130° C.; a distillation pressure can be from about 20 mbara (about 2 kPa (absolute)) to about 500 mbara ((about 50 kPa (absolute)), such as from about 50 mbara ((about 5 kPa (absolute)) to about 200 mbara ((about 20 kPa (absolute)); or combinations thereof. Any of the foregoing numbers can be used singly to describe an open-ended range or in combination to describe a close-ended range. Other temperatures and pressures for distillation are contemplated depending on the epihalohydrin used.

Another method can include evaporating epihalohydrin (and optionally other volatile components) from the resin mixture using a flash evaporator, falling film evaporator, boiling tube evaporators, wiped film evaporator, stripping columns, stripping with intern gasses, stripping with steam, or other suitable techniques. Combinations of removal operations can be performed.

After the removal of unreacted epihalohydrin by the removal process of operation 320, the resin mixture can comprise, consist essentially of, or consist of a desired glycidyl ether (an epoxy resin composition), the LER added, and residual salt formed from the glycidation reaction.

As opposed to conventional processes that would not be suitable with biologically-derived substrates (or other unconventional substrates), embodiments described herein utilize the addition of a LER to the second composition to enable, for example, feeding the second composition (as a resin mixture) to a separate unit where further operations (such as the work-up sub-process 215, including the finishing reaction of optional operation 325 described below) can be performed. In contrast, conventional processes would observe the gelling or solidification of the product from the glycidation reaction. In addition, the use of a LER helps solubilize components of the second composition (for example, glycidyl ethers and by-products made from unconventional substrates) in organic solvents when such components would have otherwise been insoluble by conventional processes. Here, insolubility of components of the second composition formed by conventional processes would have, for example, prevented feeding of the second composition to a separate reactor for work-up, and prevented further processing as gelling or solidification would have rendered mixing impossible (or at least difficult and inefficient). Further, the insolubility would have prevented subsequent ring-closure reaction of the halohydrin reaction product (for example, a halohydrin reaction product of formula (V-2)) as the halohydrin reaction product would need to be in solution to react with an alkaline reagent to effect the ring closure. That is conventional processes would be unable to use, for example, biologically-derived materials or resin waste/recycle streams as substrates.

Here, solubility means that the one or more components (for example, glycidyl ethers and halohydrin reaction product made from unconventional substrates) can be in the form of a slurry, with the one or more components partially or completely dissolved.

In embodiments that utilize a single reactor, vessel, or unit for the formation of the epoxy resin composition from unconventional substrates (for example, one reactor for both the reaction sub-process 205 and the work-up sub-process 215), the LER can keep the glycidyl ether and halohydrin reaction product in the second composition from gelling or solidifying. By keeping these materials from gelling or solidifying, the halohydrin reaction product can react to ring close and form the glycidyl ether in higher yield.

In some embodiments, and after operation 320, the resin mixture can optionally be processed to separate the salt formed from the glycidation reaction. Here, for example, the salt can be removed from the resin mixture by any suitable method such as filtration, centrifugation or other solid/liquid separation techniques. Additionally, or alternatively, the salt can be separated from the resin mixture by adding an organic solvent and water to the resin mixture. The water dissolves the salt and the resulting aqueous and organic phases can be separated. Suitable organic solvents used for the separation include ketones, aromatic hydrocarbons, and halogenated aliphatic compounds such as, for example, methyl isobutyl ketone, methyl ethyl ketone, toluene, xylene, methylene chloride, ethylene dichloride, or mixtures thereof, among others. Combinations of solvents can be used. The amount of organic solvent and water used for the separation may vary widely depending on the solvent utilized and the properties of the resin mixture, among other factors.

As an illustrative, but non-limiting, example of a phase separation, an amount of organic solvent utilized may be from about 25 wt % to about 75 wt %, such as from about 40 wt % to about 60 wt % when used in combination with the resin mixture to provide a total weight of the solvent and resin mixture of 100 wt %, though other amounts are contemplated. An amount of water is added to dissolve the salt. The amount of water utilized can be based on the salt-water solution formed, such as an amount of water to form a salt-water solution of about 0.1 wt % to about 30 wt %, such as from about 1 wt % to about 26 wt %, such as from about 5 wt % to about 23 wt %, such as from about 15 wt % to about 20 wt % of salt in the water, though other amounts are contemplated. After addition of the organic solvent and the water, the mixture stratifies into an aqueous brine phase and an organic resin-containing phase and the two phases are separated.

Separation of the organic phase and the aqueous phase may be accomplished via any suitable liquid-liquid separation, including decanters, coalescers, and decanting centrifuges, among others.

Operation 320 can optionally include utilizing a non-reactive gas, such as nitrogen, argon, or combinations thereof. For example, a non-reactive gas can be used to remove residual solvent or residual epihalohydrin excesses from the reaction mixture during operation 320.

Referring back to FIG. 3, the process 300 can further include optionally converting residual halohydrin reaction product to a third composition comprising an epoxy resin composition at optional operation 325. As described herein, the resin mixture formed from operation 320 can include a halohydrin reaction product in addition to epoxy resin composition. The reaction of optional operation 325 is then performed to, for example, complete the dehydrohalogenation of residual halohydrin reaction product (for example, a halohydrin reaction product of formula (V-2)) and form the ring-closed product as the desired glycidyl ether (such as a glycidyl ether of formula (V-1)). When there is residual halohydrin reaction product left, there is typically only about 10% or less.

The conversion reaction of optional operation 325 is referred to herein as a “finishing reaction”. The finishing reaction can include forming a mixture comprising the second composition, an alkaline reagent, and a solvent, and reacting the mixture, under reaction conditions. Suitable alkaline reagents and solvents useful for optional operation 325 include those alkaline reagents and solvents described herein, among others.

When the reaction of operation 310 does not result in a composition having a halohydrin reaction product (for example, a halohydrin reaction product of formula (V-2)), the process can be free of optional operation 325. Additionally, or alternatively, epoxy resin compositions comprising residual halohydrin reaction product can be used as is.

In some embodiments, an amount of residual halohydrin reaction product in an epoxy resin composition can be about 10% or less, about 5 wt % or less, about 1 wt % or less, about 0.5 wt % or less, or about 0.3 wt % or less, based on a total weight of the epoxy resin composition.

When the process 300 includes the optional salt separation, the organic solvent used for the salt separation can be utilized as the solvent for the finishing reaction of optional operation 325. Suitable organic solvents used for the finishing reaction of optional operation 325 include ketones, aromatic hydrocarbons, and halogenated aliphatic compounds such as, for example, methyl isobutyl ketone, methyl ethyl ketone, toluene, xylene, methylene chloride, ethylene dichloride, or mixtures thereof, among others. Combinations of solvents can be used.

An amount of organic solvent used for the finishing reaction of optional operation 325 can be from about 25 wt % to about 80 wt %, such as from about 30 wt % to about 70 wt %, such as from about 45 wt % to about 65 wt %, the weight percent based on a total wt % of the resin mixture and the solvent, the total wt % not to exceed 100 wt %. Any of the foregoing numbers can be used singly to describe an open-ended range or in combination to describe a close-ended range. Other amounts of solvent are contemplated.

The alkaline reagent utilized for the finishing reaction of optional operation 325 can be the same as those alkaline reagents described herein, such as an alkali metal hydroxide, an alkali earth metal hydroxide, or combinations thereof. Mixtures of alkaline reagents (for example, NaOH and KOH) can be utilized if desired.

An amount of alkaline reagent used for the finishing reaction of optional operation 325 can be any suitable quantity, such as a quantity that will suitably ring close of the residual halohydrin reaction product. In some embodiments, the amount of alkaline reagent is from about 1 wt % to about 10 wt % such as from about 2 wt % to about 8 wt %, such as from about 3 wt % to about 5 wt %, based on a total amount of alkaline reagent, resin mixture, and the solvent, the total not to exceed 100 wt %. Any of the foregoing numbers can be used singly to describe an open-ended range or in combination to describe a close-ended range. Other amounts are contemplated. The catalyst can be added to the resin mixture and the solvent as a solid or as a solution.

The reaction conditions of the finishing reaction of optional operation 325 can include a dosing time (or injection time), a post-dosing time (or a post-injection time) and a total reaction time. The dosing time of the finishing reaction is the period over which the alkaline reagent is added to the resin mixture and the solvent. The dosing time of the finishing reaction of optional operation 325 can be from about 10 minutes to about 5 hours, such as from about 40 minutes to about 4 hours, such as from about 1 hour to about 3 hours, though other periods are contemplated. Any of the foregoing numbers can be used singly to describe an open-ended range or in combination to describe a close-ended range.

The post-dosing time of the finishing reaction of optional operation 325 is the period after all of the alkaline reagent is dosed during optional operation 325 to the conclusion of the finishing reaction of optional operation 325. The conclusion of the finishing reaction can be based on the time point at which a certain percent conversion of the substrate has occurred. The conclusion of the finishing reaction can be based on the time point at which a certain percent conversion of the halohydrin reaction product has occurred. For example, the post-dosing time of the finishing reaction of optional operation 325 can be the amount of time between the conclusion of the dosing time and the point at which about 70% or more conversion of the residual halohydrin reaction product has occurred, such as about 75% or more conversion, such as about 80% or more conversion, such as about 85% or more conversion, such as about 90% or more conversion, such as about 95% or more conversion, such as about 96% or more conversion, such as about 97% or more conversion, such as about 98% or more conversion, such as about 99% or more conversion, though other amounts of conversion are contemplated. Any of the foregoing numbers can be used singly to describe an open-ended range or in combination to describe a close-ended range. In some examples, the post-dosing time of optional operation 325 can be from about 20 minutes to about 4 hours, such as from about 40 minutes to about 3 hour, such as from about 1 hour to about 2 hours, though other periods are contemplated. Any of the foregoing numbers can be used singly to describe an open-ended range or in combination to describe a close-ended range.

The total reaction time of the finishing reaction of optional operation 325 is the sum of the dosing and the post-dosing times of optional operation 325. In some embodiments, the total reaction time of the finishing reaction of optional operation 325 can be from about 0.5 hours to about 8 hours, such as from about 1.5 hours to about 6 hours, from about 2.5 to about 4.5 hours, from about 0.5 hours to about 8 hours, or from about 1 hour to about 3 hours, though other periods are contemplated. Any of the foregoing numbers can be used singly to describe an open-ended range or in combination to describe a close-ended range.

The reaction conditions of the finishing reaction of optional operation 325 can include a reactor temperature that is from about 20° C. to about 100° C., such as from about 35° C. to about 95° C., such as from about 50° C. to about 90° C., though other temperatures are contemplated. Any of the foregoing numbers can be used singly to describe an open-ended range or in combination to describe a close-ended range. The reactor temperature is the temperature monitored by a temperature probe.

The reaction conditions of the finishing reaction of optional operation 325 can also include a reactor pressure as measured in units of absolute pressure. The reactor pressure can be from about 1 bara (about 100 kPa (absolute)) to about 20 bara ((about 2000 kPa (absolute)), such as from about 2bara ((about 200 Pa (absolute)) to about 15 bara ((about 1500 Pa (absolute)), from about 5 bara ((about 500 kPa (absolute)) to about 10 bara ((about 1000 kPa (absolute)), or from about 7 bara ((about 700 kPa (absolute)) to about 9bara ((about 900 kPa (absolute)), though other pressures are contemplated. Any of the foregoing numbers can be used singly to describe an open-ended range or in combination to describe a close-ended range.

The reaction conditions of the finishing reaction of optional operation 325 can include stirring, mixing, agitation, or combinations thereof. The apparatus used to perform stirring, mixing or agitation can include a batch reaction vessel, a semi-batch reaction vessel, a continuous static mixer, or other suitable apparatus. Mechanical agitation or jet mixing can be used. In some embodiments, water can be removed (for example, continuously or periodically) from the organic phase by, for example, distillation during at least a portion of the finishing reaction of optional operation 325. The distillation can be an azeotropic distillation such that the reaction water is removed from the organic phase.

The reaction conditions of the finishing reaction of optional operation 325 can optionally include utilizing a non-reactive gas, such as nitrogen, argon, or combinations thereof. For example, the mixture comprising the resin mixture, catalyst, and solvent can be used with these or other non-reactive gases to degas various components or otherwise remove oxygen from the mixture.

At this stage (after optional operation 325), a third composition is provided. The third composition comprises, consists of, or consists essentially of an epoxy resin composition, and optionally, one or more additional components. The epoxy resin composition comprises, consists of, or consists essentially of a glycidyl ether (as an example desired product, for example, a glycidyl ether of formula (V-1)). This glycidyl ether can comprise the glycidyl ether made during operation 305, the glycidyl ether made during operation 310, the glycidyl ether made during optional operation 325, or combinations thereof. The one or more additional components in the third composition can comprise, consist essentially of, or consist of, solvent, salt, water, combinations thereof, among other components such as residual halohydrin reaction product. The finishing reaction also produces small amounts of water and this water can be left in the reaction mixture until the end of the finishing reaction and removed via washing, liquid-liquid separation.

In some embodiments, and after optional operation 325, the third composition can be subjected to optional operations to recover, or otherwise purify, epoxy resin composition present in the third composition. For example, salt can be removed from the third composition by any suitable method such as filtration, centrifugation or other solid/liquid separation techniques. Additionally, or alternatively, the salt can be separated from the third composition by adding an organic solvent and water to the third composition. The water dissolves the salt and the resulting aqueous and organic phases can be separated. Suitable organic solvents used for the separation include ketones, alcohols, aromatic hydrocarbons, and halogenated aliphatic compounds such as, for example, methyl isobutyl ketone, methyl ethyl ketone, isopropanol, ethanol, methanol, toluene, xylene, methylene chloride, ethylene dichloride, or mixtures thereof, among others. Combinations of solvents can be used. The amount of organic solvent and water used for the separation may vary widely depending on the solvent utilized and the properties of the third composition, among other factors. Separation of the organic phase and the aqueous phase can be accomplished via any suitable liquid-liquid separation, including decanters, coalescers, and decanting centrifuges, among other techniques. Multiple separation operations can be performed if desired.

As an illustrative, but non-limiting, example, water can be added to the third composition and the resulting biphasic mixture can be stirred. Stirring can be stopped and the mixture stratifies into an aqueous brine phase and an organic resin-containing phase. The two phases can be separated via any suitable liquid-liquid separation, including decanters, coalescers, and decanting centrifuges, among other techniques. Multiple separation operations can be performed if desired.

Besides an optional salt separation, water and organic solvent can be optionally removed from the third composition. The removal of water and organic solvent is largely governed by the organic solvent present. Removal of water and organic solvent can be performed by, for example, evaporation or distillation (under suitable conditions), among other methods. Here, for example, and depending on the materials to be removed, a distillation temperature can be from about 50° C. to about 150° C., such as from about 70° C. to about 160° C., such as from about 80° C. to about 130° C.; a distillation pressure can be from about 20 mbara (about 2 kPa (absolute)) to about 500 mbara ((about 50 kPa (absolute)), such as from about 100 mbara ((about 10 kPa (absolute)) to about 400 mbara ((about 40 kPa (absolute), such as from about 200 mbara ((about 20 kPa (absolute)) to about 300 mbara ((about 30 kPa (absolute)); or combinations thereof. Any of the foregoing numbers can be used singly to describe an open-ended range or in combination to describe a close-ended range. Other temperatures and pressures for distillation are contemplated depending on the epihalohydrin used. Multiple removal operations can be performed.

The residue remaining after the optional separation/removal operations is an epoxy resin composition (for example, the desired glycidyl ether).

In some embodiments, processes for forming a resin composition such as an epoxy resin composition (for example, process 300) can be performed according to the following non-limiting procedure. A mixture of a substrate (or glycidation substrate) comprising an alcohol (such as bisphenol A), an epihalohydrin (such as epichlorohydrin, ECH), and a solvent (such as organic solvents described herein, such as an alcohol, for example, isopropanol) can be loaded into a reactor. The reactor can be set to a temperature of about 50° C. to about 95° C. and a pressure of about 300 mbara ((about 30 kPa (absolute)) to about 500 mbara ((about 50 kPa (absolute)). The glycidation can be started by dosing a catalyst (such as tetramethyl ammonium chloride) and an alkaline reagent (such as sodium hydroxide) and continuously removing water and ECH from the reactor by azeotropic distillation. The ECH can be recycled back to the reactor. The reaction product forms and can include glycidated substrate, a halohydrin reaction product, and salt. After a desired amount of time or level of conversion of the substrate to the reaction product, a liquid epoxy resin (such as Epikote 828) is added to the reaction mixture containing the reaction product. The formed resin mixture comprising the glycidated substrate, halohydrin reaction product, salt, and unreacted ECH is subjected to a distillation to remove the unreacted ECH. The aforementioned process can be reaction sub-process 205.

The resin mixture can be discharged from the reactor (via a line, for example, line 210) and pumped to a different reactor where the work-up sub-process (for example, work-up sub-process 215) can occur. An organic solvent such as methyl isobutyl ketone (MIBK) is added to the resin mixture and a water wash is performed to remove the salt from the resin mixture. The aqueous phase is separated from the organic phase. The organic phase, which includes at least a portion of the resin mixture, is then subject to the finishing reaction. Here, the reactor can be set to a temperature of about 50° C. to about 95° C. and a pressure of about 700 mbara ((about 70 kPa (absolute)) to about 1100 mbara ((about 110 kPa (absolute)). The finishing reaction can be started by dosing an alkaline reagent (such as sodium hydroxide). The halohydrin reaction product of the resin mixture ring closes to form the desired glycidated product. The composition comprising the glycidated product also includes salt which can be removed by adding an organic solvent (for example MIBK), washing with water, and retrieving the organic phase. The organic phase can then be subjected to distillation to remove residual organic solvent and water to provide an epoxy resin composition. The resulting epoxy resin composition can be a liquid epoxy resin.

Resin compositions (for example, the resin composition formed by process 300) may be used to make any suitable type of polymer in which an epoxide reactant is typically used, including, for example, polymers for use in the coatings, composites, or adhesives industries.

The resin compositions formed by processes described herein can be used as binders, paints, sealants, among other applications. For example, the compositions can be used in construction, with installation of concrete and cement, such as high-gloss concrete installations. Another use includes coating metals. Other end-use applications for the compositions described herein include, but are not limited to: cellulosic, lignocellulosic, and wood products; plastics; fabrics (wovens and non-wovens); and glass. The resin compositions can be used generally for producing composites, adhesives, insulation materials, shaped products, binders, laminates, among other articles and articles of manufacture.

Embodiments described herein also relate to processes for separating desired and usable substrates from raw materials, waste streams, and recycle streams. As described above, unconventional substrates often originate from mixtures that are very crude and have complex composition. For example, alcohols of biological origin may come from a lignin source or a lignin waste stream (such as technical lignin, Kraft lignin, organosolv lignin, hydrolysis lignin, among others) and alcohols present in an epoxy resin or phenolic resin may come from recycled epoxy resins and phenolic resins, respectively. Unlike conventional technologies for extracting alcohols (for example, glycidation substrates) from complex mixtures, such as crude materials of biological origin and recycled or waste streams of epoxy resins and phenolic resins, embodiments described herein can be free of depolymerization operations. Further, embodiments described herein can be free of separation or fractionation techniques that involve, at least, the use of solvents that are not used for downstream glycidation processes. However, it is contemplated that embodiments described herein can be used with depolymerization operations and separation or fractionation techniques that use solvents.

Embodiments of the separation processes described herein (for example, process 400 and process 500, below) utilize an epihalohydrin as an extraction agent to solubilize desired substrates present in crude raw materials. To the inventors' knowledge, epihalohydrins (such as epichlorohydrin) have not been used as an extraction agent or extraction solvent, due to, for example, its relatively high reactivity. Epihalohydrin is not considered a typical extraction solvent and would not be considered as an attractive choice among all other available solvent, due to, for example, difficulties to work with it. However, as epihalohydrins are utilized in the production of epoxy resin compositions, the use of it as an extraction agent/solvent to separate desired substrates from crude raw materials, waste streams, and recycle streams to use for subsequent glycidation can provide advantages.

In addition, use of epihalohydrin to extract the substrate for glycidation from the substrate source guarantees that the solubility of the substrate for downstream glycidation operations, where often only epihalohydrin is used as solvent and reagent. Such a guarantee is not obtained when using other solvents, as the solubility of the extracted fraction might still be low in epihalohydrin, making downstream glycidation cumbersome and very difficult to operate.

Further, as epihalohydrins are used to extract desired substrate(s) from crude materials, no additional solvent is required to produce epoxy resins as epihalohydrins are used to produce the epoxy resins. Here, embodiments described herein can be free of complex additional separation processes and storage facilities as would be needed if a solvent other than an epihalohydrin is to be used. Accordingly, production costs and lower energy costs can be realized. This can be especially true when the epihalohydrin is not removed after the extraction (or separation) of desired substrates such as phenolic materials from the substrate source and the mixture of epihalohydrin and desired substrate is used as is for glycidation reactions.

Additionally, the separation processes can be applied to various types of alcohols (such as alkyl alcohols, polyhydric alcohols, phenols, and polyhydric phenols). The separation processes can be free of complex catalysts, complex parameters, and complex equipment, as is the case for other fractionation technologies and depolymerization technologies.

Embodiments described for the separation of substrates (for example, alcohols and phenols) from complex mixtures can be combined with embodiments for forming glycidyl ethers. Further, processes for separating substrates (for example, alcohols and phenols) from complex mixtures can be combined with conventional processes for forming glycidyl ethers. That is, the substrates separated by embodiments described herein can be fed to downstream upgrading processes such as conversion to epoxy resin compositions among other upgrading processes.

Figure 4:
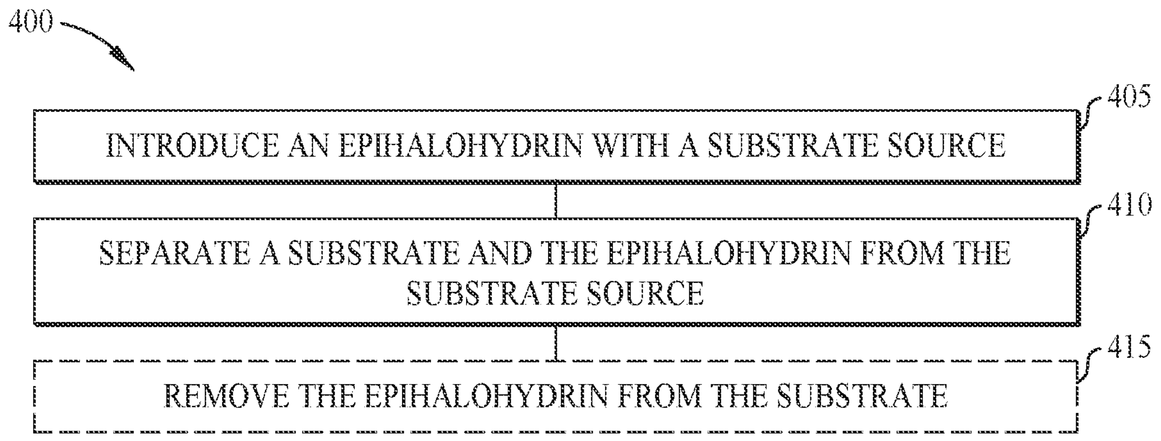
FIG. 4 is a flowchart showing selected operations of a process for separating a substrate from a substrate source according to at least one embodiment of the present disclosure.

FIG. 4 is a flowchart showing selected operations of a process 400 for separating a substrate from a substrate source according to at least one embodiment of the present disclosure.

The process 400 includes introducing an epihalohydrin with a substrate source at operation 405. Suitable substrate sources for operation 405 can include raw materials, waste streams, or recycle streams, among other mixtures and complex mixtures. Such substrate sources can include any suitable substrate source that comprises, consists essentially of, or consists of substrates (compounds) comprising at least one hydroxyl (—OH) group. That is, the substrate source used in operation 405 can contain substrates or compounds such as alcohols, polyhydric alcohols, phenols, and polyhydric phenols. Such substrate sources can be of biological origin or non-biological origin.

The substrate sources can be mixtures of complex composition. As mixtures or complex mixtures, the substrate sources include undesirable materials or components such as polymers of very high molecular weight, insolubles, salts, among other materials and components. Such undesirable materials or components are typically present in Kraft lignins, hydrolytic lignins, recycle streams coming from pyrolysis or solvolysis processes, among other substrate sources.

Figure 5:
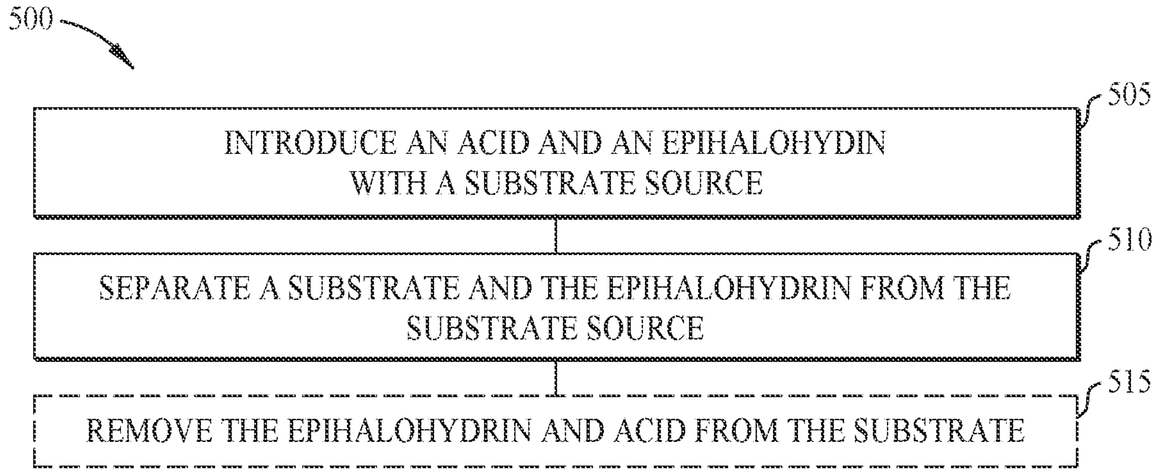
FIG. 5 is a flowchart showing selected operations of a process for separating a substrate from a substrate source according to at least one embodiment of the present disclosure.

Although embodiments described herein with reference to FIG. 4 and FIG. 5 are discussed with reference to phenols, polyhydric phenols or phenol moieties for simplicity, it should be understood that any suitable substrate comprising at least one hydroxyl (—OH) group can be used, such as alkyl alcohols and aliphatic alcohols (where the hydroxyl group is attached to a non-aromatic carbon), as well as aromatic alcohols (such as phenols where the hydroxyl group is attached to an aromatic carbon).

Substrate sources useful with embodiments described herein can include biomass. Illustrative, but non-limiting, examples of biomass include materials, by-products, and waste generated from, e.g., agricultural and forestry processes, such as agricultural matter and residues (e.g., wheat straw and corn), energy crops (e.g., wheatgrass and bamboo), forest residues (e.g., materials, by-products and waste from forest harvesting such as woodchips), plant- and algae-based matter and residues, and the like, and combinations thereof. In some embodiments, biomass includes wood, leaves, pulps, stalks, grass material, shrubs, branches, energy crops, vegetables, fruits, flowers, grains, herbaceous crops, bark, needles, logs, trees, and combinations thereof. Additionally, or alternatively, biomass includes municipal solid waste, by-products and waste from wood-processing, by-products and waste from papermaking or timber processes, by-products and waste from agricultural and forestry activities, rotation crops, lumber, wood chips, sawdust, straw, firewood, wood materials, paper, waste paper, yard waste, and the like. Accordingly, alcohols (for example, polyhydric phenols) present in such materials (biomass) can be used with embodiments described herein.

Suitable substrate sources for operation 405 include any suitable lignin source including lignin sources that may not be fully soluble in epihalohydrin. Suitable substrate sources for operation 405 include technical lignin, Kraft lignin, organosolv lignin, hydrolysis lignin, combinations thereof, among other lignin sources. Technical lignin refers to native lignin or proto-lignin derivative obtained as the result of the delignification process of lignocellulosic biomass. Kraft lignin refers to an industrial lignin obtained from Kraft pulp by the Kraft process for converting a bio-based substrate (for example, one of those above, such as wood) to pulp. Organosolv lignin refers to lignin obtained by organosolv, a pulping technique that uses an organic solvent to solubilize lignin and hemicellulose. Hydrolysis lignin refers to a by-product from pretreatment processes such as those in cellulosic ethanol plants, and typically includes lignin, unreacted cellulose, monosaccharides, and oligosaccharides. Besides lignins, other suitable phenolic-rich fractions can be substrate sources for operation 405.

Suitable substrate sources for operation 405 include waste streams and recycle streams comprising resins such as epoxy resins, phenolic resins, or combinations thereof, among other resins. Such waste streams and recycle streams can come from pyrolysis or solvolysis processes designed for recycling polymer wastes. These waste streams and recycle streams include alcohols (such as phenols and alkyl alcohols) that can be separated. Such waste streams and recycle streams can be those waste/recycle streams used or made during processing or manufacturing of resins. Mixtures of substrate sources can be used as the substrate source for process 400.

Suitable epihalohydrins for use in operation 405 include those represented by formula (VI):

(VI)

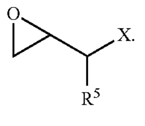

In formula (VI), $R^5$ is a hydrogen, an unsubstituted hydrocarbyl, or a substituted hydrocarbyl. The $R^5$ group of epihalohydrin shown in formula (VI) can include from 1 to 20 carbon atoms, such as from 1 to 10 carbon atoms, such as from 1 to 4 carbon atoms. The X group in formula (VI) is a halogen such as fluorine, chlorine, bromine, or iodine, such as chlorine or bromine. In some embodiments, the epihalohydrin comprises epichlorohydrin (X=Cl and $R^5$=H in formula (VI); CAS No. 106-89-8), epibromohydrin (X=Br and $R^5$=H in formula (VI); CAS No. 3132-64-7), or combinations thereof.

In some embodiments, a mass ratio of the substrate source to the epihalohydrin used for process 400 is from about 10:1 to about 1:10, such as from about 5:1 to about 1:5, such as from about 3:1 to about 1:3, such as from about 2:1 to about 1:2, such as about 1:1. In at least one embodiment, a mass ratio of the substrate source to the epihalohydrin is from about 1:1 to about 1:10, such as from about 1:2 to about 1:9, such as from about 1:3 to about 1:8, such as from about 1:4 to about 1:7, such as from about 1:5 to about 1:6. Other mass ratios are contemplated. Any of the foregoing numbers can be used singly to describe an open-ended range or in combination to describe a close-ended range.

Introduction of the epihalohydrin with the substrate causes contact of at least a portion of the epihalohydrin with a desired substrate present in the substrate source, enabling the desired substrate to be separated.

Operation 405 can further include a mixing sub-process. The mixing sub-process of operation 405 can include any suitable conditions to enable sufficient contact of the substrate source with epihalohydrin. For example, the epihalohydrin and the substrate source can be stirred, mixed, agitated, or combinations thereof, using any suitable apparatus. An apparatus used to perform stirring, mixing, or agitation can include a batch reaction vessel, a semi-batch reaction vessel, a continuous static mixer, or other suitable apparatus. Mechanical agitation or jet mixing can be used.

Conditions effective of the mixing sub-process of operation 405 can also include mixing, stirring, or agitating the mixture at selected temperatures and pressures. For example, the vessel in which the epihalohydrin and the substrate source are located together can be set to a vessel temperature that is from about −10° C. to about 100° C., such as from about 0° C. to about 80° C., such as from about 10° C. to about 60° C., such as from about 20° C. to about 50° C., such as from about 25° C. to about 40° C., though other temperatures are contemplated. Any of the foregoing numbers can be used singly to describe an open-ended range or in combination to describe a close-ended range. The vessel temperature is the temperature monitored by a temperature probe.

The vessel pressure, as measured in units of absolute pressure, can be from about 500 mbara (about 50 kPa (absolute)) to about 3,000 mbara ((about 300 kPa (absolute)), such as from about 700 mbara ((about 70 kPa (absolute)) to about 2,500 ((about 250 kPa (absolute)), such as from about 800 mbara ((about 80 kPa (absolute)) to about 2,000 ((about 200 kPa (absolute)), such as from about 850 mbara ((about 85 kPa (absolute)) to about 1,200 mbara ((about 120 kPa (absolute)), such as from about 900 mbara ((about 90 kPa (absolute)) to about 1,100 mbara ((about 110 kPa (absolute)), such as from about 900 mbara ((about 90 kPa (absolute)) to about 1,000 mbara ((about 100 kPa (absolute)) or from about 1,000 mbara ((about 100 kPa (absolute)) to about 1,100 mbara ((about 110 kPa (absolute)), though other pressures are contemplated. Any of the foregoing numbers can be used singly to describe an open-ended range or in combination to describe a close-ended range.

A total time of mixing, stirring, or agitation during the mixing sub-process of operation 405 can be from about 10 minutes to about 24 hours, such as from about 30 minutes to about 15 hours, such as from about 1.5 hours to about 6 hours, from about 2.5 to about 4.5 hours, from about 30 minutes to about 8 hours, from about 45 minutes to about 3 hours, or from about 1 hour to about 2 hours, though other periods are contemplated. Any of the foregoing numbers can be used singly to describe an open-ended range or in combination to describe a close-ended range.

After sufficient mixing of the substrate source, the epihalohydrin, and the acid, the resultant mixture can be separated. Accordingly, the process 400 further includes separating a substrate (a desired substrate) and the epihalohydrin from the substrate source at operation 410. The substrate that is separated from the substrate source in operation 410 comprises at least one hydroxyl group, for example, an alcohol of biological origin, an alcohol present in a resin waste stream, an alcohol present in a resin recycle stream, or combinations thereof. Such alcohols can include phenols and aliphatic alcohols, among others. The substrate that is separated from the substrate source in operation 410 can be a substrate utilized in process 300 (for example, glycidation substrates).

Operation 410 is conducted under conditions effective to separate the substrate from the substrate source. The conditions of operation 410 can include any suitable conditions and techniques. For example, the separating process of operation 410 can include any suitable separation technique such as solid/liquid techniques including mechanical or gravity separation, such as filtration, vacuum filtration, centrifuges, decanters, decanter centrifuges, combinations thereof, among other techniques. Separation can be aided by pressing of the solid filter cake that forms. The separation can be performed one or more times, with optional usage of additional epihalohydrin for each filtration. Filtration can be accomplished using a porous surface to draw the filtrate (liquid containing the desired substrate) from the mixture of epihalohydrin and substrate source to one side of the porous surface, and leaving the substrate source as retentate (solid, or filter cake) on the opposite side of the substrate surface. As an example, the epihalohydrin and substrate source can be separated via, for example, filtration to provide a filtrate containing an epihalohydrin-soluble substrate, and a retentate containing an epihalohydrin-insoluble fraction.

The porous surface can be a membrane or frit made of any suitable material such as ceramic, glass, or other materials. The pores of the porous membrane can be selected to separate substrates of specific sizes or ranges (for example, weight average molecular weights or ranges) from the substrate source.

The separation process of operation 410 can be performed one or more times. After the desired number of separations, the filtrate comprising the epihalohydrin and the desired substrate is kept and the retentate (comprising the filter cake with the crude components of the substrate source) can be discarded or used for other purposes.

If desired, the resulting mixture epihalohydrin and substrate can be used directly for upgrading processes such as glycidation, such as those processes described herein for forming resin compositions.

Additionally, or alternatively, the epihalohydrin can be removed from the substrate at optional operation 415. Removing the epihalohydrin from the substrate can be accomplished by any suitable technique such as distillation or evaporation, among others. Here, for example, and depending on the epihalohydrin to be removed or other factors, optional operation 415 can include a distillation temperature that can be from about 50° C. to about 160° C., such as from about 70° C. to about 140° C., such as from about 80° C. to about 120° C., such as from about 90° C. to about 110° C.; a distillation pressure can be from about 100 mbara (about 10 kPa (absolute)) to about 700 mbara ((about 70 kPa (absolute)), such as from about 200 mbara ((about 20 kPa (absolute)) to about 500 mbara ((about 50 kPa (absolute)); or combinations thereof. Any of the foregoing numbers can be used singly to describe an open-ended range or in combination to describe a close-ended range. Other temperatures and pressures for distillation are contemplated depending on the epihalohydrin used. The removal process of optional operation 415 can be performed one or more times. The epihalohydrin can be recovered and used for other separation processes, used for glycidation reactions (for example, process 300), among other uses. After distillation, the desired substrate (a hydroxyl-containing substrate) is provided.

Additionally, or alternatively, a partial distillation can be utilized for optional operation 415 to obtain a suitable epihalohydrin/substrate ratio for the subsequent glycidation reaction. After a partial distillation, the mixture of epihalohydrin and substrate can be submitted to glycidation (for example, process 300).

In some embodiments, processes for separating a substrate comprising at least one hydroxyl group from a substrate source (for example, process 400) can be performed according to the following non-limiting procedure. A substrate source (for example, lignin) and epihalohydrin (for example, ECH) are added to a batch reaction vessel and stirred for about 1 hour at a temperature of about 25° C. and a pressure of about 1,000 mbara (about 100 kpa (absolute)). The resulting mixture is filtered with the aid of a vacuum. The filtrate containing the epichlorohydrin-soluble substrate and the ECH is distilled at a temperature of about 90° C. to about 110° C. and at a pressure of about 200 mbara (about 20 kPa (absolute)) to about 500 mbara ((about 50 kPa (absolute)) to remove the ECH from the desired substrate. The retentate contains the epihalohydrin-insoluble fraction.

Process 400 can enable hydroxyl-containing substrates (for example, glycidation substrates) to be separated from substrate sources such as raw materials, recycle streams, and waste streams. The substrates, having a hydroxyl group attached to an aromatic carbon, a hydroxyl group attached to a non-aromatic carbon (for example, an alkyl hydroxyl) can be separated. In some examples, the alcohols of biological origin and alcohols present in recycle/waste streams, and which are separated by process 400, can include polyhydric alcohols (compounds containing more than one alcohol), polyhydric phenols (compounds containing more than one phenol such as bisphenols, trisphenols, tetraphenols, and so forth), combinations thereof, among others. The substrates separated by processes described herein (for example, process 400) can be fed to downstream upgrading processes such as conversion to a resin composition (such as epoxy resin compositions, for example, by process 300), among other upgrading processes. Additionally, or alternatively, the substrates separated can be fed to conventional processes for forming resin compositions.

FIG. 5 is a flowchart showing selected operations of a process 500 for separating a substrate from a substrate source according to at least one embodiment of the present disclosure.

The process 500 includes introducing an acid and an epihalohydrin with a substrate source at operation 505. Suitable substrate sources for operation 505 can include those substrate sources described herein (for example, substrate sources utilized for operation 405 of process 400). Generally, the substrate sources for operation 505 comprise, consist essentially of, or consist of, of substrates (compounds) comprising at least one hydroxyl (—OH) group, such as alcohols, polyhydric alcohols, phenols, and polyhydric phenols. The substrate sources are of biological origin or non-biological origin.

Suitable epihalohydrins for use in operation 505 include those represented by formula (VI) described herein. For example, epichlorohydrin (X=Cl and $R^5$=H in formula (VI); CAS No. 106-89-8), epibromohydrin (X=Br and $R^5$=H in formula (VI); CAS No. 3132-64-7), or combinations thereof can be utilized.

In some embodiments, a mass ratio of the substrate source to the epihalohydrin used for process 500 is from about 10:1 to about 1:10, such as from about 5:1 to about 1:5, such as from about 3:1 to about 1:3, such as from about 2:1 to about 1:2, such as about 1:1. In at least one embodiment, a mass ratio of the substrate source to the epihalohydrin is from about 1:1 to about 1:10, such as from about 1:2 to about 1:9, such as from about 1:3 to about 1:8, such as from about 1:4 to about 1:7, such as from about 1:5 to about 1:6. Other mass ratios are contemplated. Any of the foregoing numbers can be used singly to describe an open-ended range or in combination to describe a close-ended range.

Acids used for operation 505 can include any suitable acid such as an inorganic acid, an organic acid, an ion thereof, or a combination thereof. Illustrative, but non-limiting, examples of inorganic acids include hydrochloric acid (HCl), sulfuric acid ($H_2SO_4$), nitric acid ($HNO_3$), hydrobromic acid (HBr), hydroiodic acid (HI), phosphoric acid ($H_3PO_4$), an ion thereof, or combinations thereof. Illustrative, but non-limiting, examples of organic acids include $C_1$-$C_{25}$ carboxylic acid, such as a $C_3$-$C_{10}$ carboxylic acid, such as a $C_3$-$C_7$ carboxylic acid, such as oxalic acid, citric acid, formic acid, lactic acid, acetic acid, uric acid, malic acid, tartaric acid, trifluoroacetic acid, an ion thereof, or combinations thereof. Additionally, or alternatively, sulfonic acids such as a $C_1$-$C_{25}$ sulfonic acid, such as a $C_3$-$C_{10}$ sulfonic acid, such as a $C_3$-$C_7$ sulfonic acid, such as trifluorosulfonic acid, or p-toluenesulfonic acid, or combinations thereof can be utilized. In some embodiments, the pH can be maintained at a pH value that is higher than the decomposition pH (at a specific temperature) of epihalohydrin in water. The decomposition pH of epihalohydrin in water is temperature-dependent and can be readily checked by monitoring an exotherm and measuring the temperature.

The acid solution can be added to the substrate source until the pH reaches a desired value and maintains that value such that one or more hydroxyl moieties (such as phenolic hydroxyl moieties) of the substrate sources are protonated. Here, and as described above, the temperature of the epihalohydrin in water should be monitored such that, for example, the pH is not lower than when observing an exothermic decomposition of the epihalohydrin. Suitable pH values of the acid solution can be about 7.5 or less, such as about 7 or less, such as from about 1 to about 6.5, such as from about 1 to about 5, about 2 to about 4, about 1 to about 3, or from about 2 to about 3, though other pH values or ranges are contemplated. Any of the foregoing numbers can be used singly to describe an open-ended range or in combination to describe a close-ended range. The pH can be selected such that the epihalohydrin will not be very reactive.

Use of the acid can improve the extraction yield from various substrate sources such as lignin sources such as Kraft lignin. Acidification lowers the pH such that hydroxyl moieties (such as phenolic hydroxyl moieties) of the substrate sources are protonated, and leading to higher solubilization of the desired substrates having hydroxyl moieties.

It can be problematic to use an acid in the presence of epihalohydrins due to its instability in acidic conditions. However, it was unexpectedly found that the acid can be selective for protonating the hydroxyl moieties of substrate sources rather than undergoing a ring opening of the epihalohydrin.

In some embodiments, the acid can be added as a solution at any suitable concentration in a suitable solvent (for example, water or an organic solvent, that effectively dissolves the acid(s)) such as from about 0.01 M to about 18 M, from about 0.1 M to about 9 M, from about 3 M to about 12 M, from about 6 M to about 15 M. Higher or lower concentrations can be utilized. Any of the foregoing numbers can be used singly to describe an open-ended range or in combination to describe a close-ended range.

In some embodiments, a mass ratio of the acid solution to the substrate source is from about 0.01:1 to about 1:1, such as from about 0.1:1 to about 0.5:1, such as from about 0.2:1 to about 0.4:1.

In some embodiments, the acid can be added to the substrate source prior to addition of the epihalohydrin, during addition of the epihalohydrin, after addition of the epihalohydrin, or combinations thereof. Introduction of the epihalohydrin can be performed in the same or different apparatus as that used for introducing the acid to the substrate source.

Operation 505 can further include a mixing sub-process. The mixing sub-process of operation 505 can include any suitable conditions to enable sufficient contact of the substrate source with epihalohydrin. For example, the mixture can be stirred, mixed, agitated, or combinations thereof, using any suitable apparatus. An apparatus used to perform stirring, mixing, or agitation can include a batch reaction vessel, a semi-batch reaction vessel, a continuous static mixer, or other suitable apparatus. Mechanical agitation or jet mixing can be used.

Conditions effective of the mixing sub-process of operation 505 can also include mixing, stirring, or agitating the mixture at selected temperatures and pressures. For example, the vessel can be set to a vessel temperature that is from about −10° C. to about 100° C., such as from about 0° C. to about 80° C., such as from about 10° C. to about 60° C., such as from about 20° C. to about 50° C., such as from about 25° C. to about 40° C., though other temperatures are contemplated. Any of the foregoing numbers can be used singly to describe an open-ended range or in combination to describe a close-ended range. The vessel temperature is the temperature monitored by a temperature probe.

The vessel pressure during the mixing sub-process of operation 505, as measured in units of absolute pressure, can be from about 500 mbara (about 50 kPa (absolute)) to about 3,000 mbara ((about 300 kPa (absolute)), such as from about 700 mbara ((about 70 kPa (absolute)) to about 2,500 ((about 250 kPa (absolute)), such as from about 800 mbara ((about 80 kPa (absolute)) to about 2,000 ((about 200 kPa (absolute)), such as from about 850 mbara ((about 85 kPa (absolute)) to about 1,200 mbara ((about 120 kPa (absolute)), such as from about 900 mbara ((about 90 kPa (absolute)) to about 1,100 mbara ((about 110 kPa (absolute)), such as from about 900 mbara ((about 90 kPa (absolute)) to about 1,000 mbara ((about 100 kPa (absolute)) or from about 1,000 mbara ((about 100 kPa (absolute)) to about 1,100 mbara ((about 110 kPa (absolute)), though other pressures are contemplated. Any of the foregoing numbers can be used singly to describe an open-ended range or in combination to describe a close-ended range.

A total time of mixing, stirring, or agitation during the mixing sub-process of operation 505 can be from about 10 minutes to about 24 hours, such as from about 30 minutes to about 15 hours, such as from about 1.5 hours to about 6 hours, from about 2.5 to about 4.5 hours, from about 30 minutes to about 8 hours, from about 45 minutes to about 3 hours, or from about 1 hour to about 2 hours, though other periods are contemplated. Any of the foregoing numbers can be used singly to describe an open-ended range or in combination to describe a close-ended range.

After sufficient mixing of the substrate source, the epihalohydrin, and the acid, the resultant mixture can be separated. Accordingly, process 500 further includes separating a substrate (a desired substrate) and the epihalohydrin from the substrate source at operation 510. The substrate that is separated from the substrate source in operation 510 comprises at least one hydroxyl group, for example, an alcohol of biological origin, an alcohol present in a resin waste stream, an alcohol present in a resin recycle stream, or combinations thereof. Such alcohols can include phenols and aliphatic alcohols, among others. The substrate that is separated from the substrate source in operation 510 can be a substrate utilized in process 300 (for example, glycidation substrates).

Operation 510 is conducted under conditions effective to separate the substrate from the substrate source. The conditions of operation 510 can include any suitable conditions and techniques such as those conditions described herein with respect to operation 410 of process 400. For example, the separating process of operation 510 can include any suitable separation technique such as solid/liquid techniques including mechanical or gravity separation, such as filtration, vacuum filtration, centrifuges, decanters, decanter centrifuges, combinations thereof, among other techniques. Separation can be aided by pressing of the solid filter cake that forms. The separation can be performed one or more times, with optional usage of additional epihalohydrin for each filtration. Filtration of operation 510 can be accomplished using any suitable porous surface such as those described above with respect to operation 410 of process 400.

The separation process of operation 510 can be performed one or more times. After the desired number of separations, the filtrate comprising the epihalohydrin and the desired substrate is kept and the retentate (comprising the filter cake with the crude components of the substrate source) can be discarded or used for other purposes. The filtrate can also contain acid when an acid is used.

If desired, the mixture comprising epihalohydrin and substrate can be used directly for upgrading processes such as glycidation, such as those processes described herein for forming resin compositions.

Additionally, or alternatively, the epihalohydrin can be removed from the substrate at optional operation 515. Removing the epihalohydrin from the substrate can be accomplished by any suitable techniques such as distillation or evaporation, as discussed above with optional operation 415 of process 400. Here, for example, and depending on the epihalohydrin to be removed or other factors, optional operation 415 can include a distillation temperature that can be from about 50° C. to about 160° C., such as from about 70° C. to about 140° C., such as from about 80° C. to about 120° C., such as from about 90° C. to about 110° C.; a distillation pressure can be from about 100 mbara (about 10 kPa (absolute)) to about 700 mbara ((about 70 kPa (absolute)), such as from about 200 mbara ((about 20 kPa (absolute)) to about 500 mbara ((about 50 kPa (absolute)); or combinations thereof. Any of the foregoing numbers can be used singly to describe an open-ended range or in combination to describe a close-ended range. Other ranges and values for the aforementioned variables such as temperature, pressure, and time are contemplated for optional operation 515 such as those described herein with respect to optional operation 415 of process 500.

The removal process of optional operation 515 can be performed one or more times. The epihalohydrin can be recovered and used for other separation processes, used for glycidation reactions (for example, process 300), among other uses. After distillation, the desired substrate (a hydroxyl-containing substrate) is provided.

Additionally, or alternatively, a partial distillation can be utilized for optional operation 515 to obtain a suitable epihalohydrin/substrate ratio for the subsequent glycidation reaction. After a partial distillation, the mixture of epihalohydrin and substrate can be submitted to glycidation (for example, process 300).

In some embodiments, the acid can be removed by suitable processes. For example, when the acid is volatile (such as acetic acid, HCl, among others), the excess acid can be removed via distillation. Additionally, or alternatively, when the desired substrate (a hydroxyl-containing substrate) is subjected to glycidation, the large amount of alkaline reagent added for the glycidation can quench the acid. Because the alkaline reagent can quench the acid, and in some embodiments, the process 500 can be free of an operation to remove the acid.

In some embodiments, processes for separating a substrate comprising at least one hydroxyl group from a substrate source (for example, process 500) can be performed according to the following non-limiting procedure. A substrate source (for example, lignin) can be mixed with an acetic acid solution (pH of about 3) in a batch reaction vessel. An epihalohydrin, such as epichlorohydrin, can be added and the resulting mixture can be stirred for about 1 hour at a temperature of about 25° C. and a pressure of about 1,000 mbara (about 100 kpa (absolute)). The resulting mixture can be filtered with the aid of a vacuum. The filtrate containing the substrate, the acetic acid, and the epichlorohydrin can be distilled at a temperature of about 90° C. to about 110° C. and at a pressure of about 100 mbara (about 10 kPa (absolute)) to about 500 mbara ((about 50 kPa (absolute)) to remove the epichlorohydrin and acetic acid from the desired substrate.

Process 500 can enable hydroxyl-containing substrates (for example, glycidation substrates) to be separated from substrate sources such as raw materials, recycle streams, and waste streams. The substrates, having a hydroxyl group attached to an aromatic carbon, a hydroxyl group attached to a non-aromatic carbon (for example, an alkyl hydroxyl) can be separated. In some examples, the alcohols of biological origin and alcohols present in recycle/waste streams, and which are separated by process 500, can include polyhydric alcohols (compounds containing more than one alcohol), polyhydric phenols (compounds containing more than one phenol such as bisphenols, trisphenols, tetraphenols, and so forth), combinations thereof, among others. The substrates separated by processes described herein (for example, process 500) can be fed to downstream upgrading processes such as conversion to a resin composition (such as epoxy resin compositions, for example, by process 300), among other upgrading processes. Additionally, or alternatively, the substrates separated can be fed to conventional processes for forming resin compositions.

Separation processes described herein (for example, process 400 and process 500) can be used to extract hydroxyl-containing substrates (for example, alcohols, polyhydric alcohols, phenols, polyhydric phenols, or combinations thereof) of various molecular weights.

The following examples are put forth so as to provide those of ordinary skill in the art with a complete disclosure and description of how to make and use embodiments of the present disclosure, and are not intended to limit the scope of embodiments of the present disclosure. Efforts have been made to ensure accuracy with respect to numbers used but some experimental errors and deviations should be accounted for.

EXAMPLES

Test Methods

Characterization of Products Formed from Example Processes

The epoxy group content (EGC) is determined according to ASTM D1652-11. This method allows to determine 1,2-epoxy group in epoxy resins in the range of 200 to 8000 mmol/kg. Perchloric acid is used as the titrant along with a quaternary ammonium halide, tetraethylammonium bromide (TEAB). For the EGC titrations, the required mass of test sample is dissolved in a fixed amount of DCM and acetic acid with the addition of an excess of TEAB. The solution was titrated with 0.01 M perchloric acid in acetic acid until an inflection point was reached. The volume of perchloric acid dosed was used to calculate the amount of epoxy functionality in mmol/kg.

The hydrolyzable chlorine and inorganic chlorine are determined according to ASTM-D1726. This method describes the determination of hydrolyzable chlorine in epoxy resins, in concentrations down to 7 mg/kg. For the titration, the required mass of test sample (after dissolving in tetrahydrofuran if it is a solid resin) is mixed with fixed amounts of toluene and 0.1 mol/L methanolic potassium hydroxide solution. Subsequently, the solution is refluxed for a specified time. After addition of acetic acid the liberated chloride is titrated potentiometrically with standard silver nitrate solution and the hydrolyzable chlorine content of the sample is calculated from the data obtained.

The viscosity of the epoxy resins is determined according to ASTM D-445. This method describes the standard test method to measure the kinematic viscosity, ν, of petroleum products.

Example 1: Glycidation

Glycidation was performed with the addition of LER after the reaction sub-process to enable the work up sub-process. The generalized reaction scheme for the glycidation of lignin phenolic moieties (an example alcohol-containing substrate) to lignin glycidyl ether moieties is shown in Scheme 2. In Scheme 2, A is the lignin phenolic moiety, B is the halohydrin reaction product, and C is the lignin glycidyl ether. L refers to lignin, Ra and Rb are R groups described herein, and the alkaline reagent is aqueous sodium hydroxide (stoichiometric).

Scheme 2

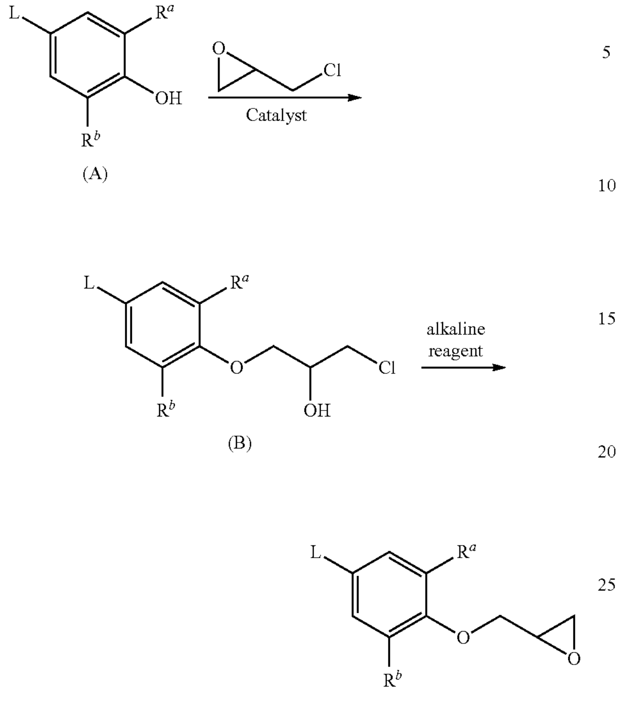

(A)

(B)

(C)

Example 1A. For this glycidation experiment, a polyhydric phenol of biological origin was used as the substrate (extracted Kraft lignin #1). Here, the substrate was removed from the substrate source (Kraft lignin) by extraction as described herein and as shown in the non-limiting Example 2, below.

Synthesis of the glycidyl ethers of Example 1A was performed according to the following procedure. The polyhydric phenol (about 5 g) and a stoichiometric excess of epichlorohydrin (about 20 g) was added to a 100 mL round bottom flask fitted with an overhead condenser. The resultant mixture was stirred using a magnetic stirrer at about 450 rpm and the reactor was heated to a desired reaction temperature (about 70° C.). A coupling catalyst, tetrabutyl ammonium chloride (TBAC, about 50% aqueous solution, about 0.4 g), was added and the reaction mixture was stirred for about 30 minutes. Sodium hydroxide (about 50% aqueous solution, about 2.6 g) was then dosed to the reaction mixture over a period of about 2 hours. The reaction mixture was allowed to continue stirring for about 30 minutes of post-reaction time. A liquid epoxy resin (Epikote 862, about 5.5 g) was added to the reaction mixture in a weight ratio of about 1:1 with respect to the epoxy product formed. Excess epichlorohydrin and water were removed using rotary evaporation. Solvent and water were added to the mixture, the mixture was stirred, and the phases were separated. Water washing was repeated twice more to remove more water soluble components. Solvent was removed from the organic phase by rotary evaporation (about 90° C. and about 60 mbar). The sample was then heated in an oven to about 120° C. and stripped with nitrogen for about 30 minutes to afford the glycidyl ether of biological origin.

Example 1B. For this glycidation experiment, a polyhydric phenol of biological origin was used as the substrate (extracted Kraft lignin #1). Here, the substrate was removed from the substrate source (Kraft lignin) by extraction as described herein and as shown in the non-limiting Example 2, below.

Synthesis of the glycidyl ethers of Example 1B was performed according to the following procedure. The polyhydric phenol (about 25 g) and a stoichiometric excess of epichlorohydrin (about 100 g) was added to a round bottom flask fitted with an overhead condenser. The resultant mixture was stirred using a magnetic stirrer at about 450 rpm and the reactor was heated to a desired reaction temperature (about 70° C.). A coupling catalyst, tetramethyl ammonium chloride (TMAC, about 50% aqueous solution, about 2 g), was added and the reaction mixture was stirred for about 30 minutes. Sodium hydroxide (about 50% aqueous solution, about 13.0 g) was then dosed to the reaction mixture over a period of about 2 hours. The reaction mixture was allowed to continue stirring for about 30 minutes of post-reaction time. A liquid epoxy resin (Epikote 862, about 27.8 g) was added to the reaction mixture in a weight ratio of about 1:1 with respect to the epoxy product formed. Excess epichlorohydrin and water were removed using rotary evaporation. Solvent and water were added to the mixture, the mixture was stirred, and the phases were separated. Water washing was repeated twice more to remove more water soluble components. Solvent was removed from the organic phase by rotary evaporation (about 90° C. and about 60 mbar). The sample was then heated in an oven to about 120° C. and stripped with nitrogen for about 30 minutes to afford the glycidyl ether of biological origin.

Example 1C. For this glycidation experiment, a polyhydric phenol of biological origin was used as the substrate (acidified extracted Kraft lignin #3). Here, the substrate was removed from the substrate source (Kraft lignin) by extraction with acidification as described herein and as shown in the non-limiting Example 2, below.

Synthesis of the glycidyl ethers of Example 1C was performed according to the following procedure. The polyhydric phenol (about 5 g) and a stoichiometric excess of epichlorohydrin (about 20 g) was added to a round bottom flask fitted with an overhead condenser. The resultant mixture was stirred using a magnetic stirrer at about 450 rpm and the reactor was heated to a desired reaction temperature (about 70° C.). A coupling catalyst, TMAC (about 50% aqueous solution, about 0.4 g), was added and the reaction mixture was stirred for about 30 minutes. Sodium hydroxide (about 50% aqueous solution, about 1.72 g) was then dosed to the reaction mixture over a period of about 2 hours. The reaction mixture was allowed to continue stirring for about 30 minutes of post-reaction time. A liquid epoxy resin (Epikote 862, about 5.5 g) was added to the reaction mixture in a weight ratio of about 1:1 with respect to the epoxy product formed. Excess epichlorohydrin and water were removed using rotary evaporation. Solvent and water were added to the mixture, the mixture was stirred, and the phases were separated. Water washing was repeated twice more to remove more water soluble components. Solvent was removed by rotary evaporation (about 90° C. and about 60 mbara). The sample was then heated in an oven to about 120° C. and stripped with nitrogen for about 30 minutes to afford the glycidyl ether of biological origin.

Example 1D. For this glycidation experiment, a polyhydric phenol of biological origin was used as the substrate (acidified, extracted kraft lignin #3). Here, the substrate was removed from the substrate source (Kraft lignin) by extraction with acidification as described herein and as shown in the non-limiting Example 2, below.

Synthesis of the glycidyl ethers of Example 1D was performed according to the following procedure. The polyhydric phenol (about 30 g) and a stoichiometric excess of epichlorohydrin (about 120 g) was added to a round bottom flask fitted with an overhead condenser. The resultant mixture was stirred using a magnetic stirrer at about 450 rpm and the reactor was heated to a desired reaction temperature (about 70° C.). A coupling catalyst, TMAC (about 50% aqueous solution, about 2.4 g), was added and the reaction mixture was stirred for about 30 minutes. Sodium hydroxide (about 50% aqueous solution, about 12 g) was then dosed to the reaction mixture over a period of about 2 hours. The reaction mixture was allowed to continue stirring for about 30 minutes of post-reaction time. A liquid epoxy resin (Epikote 862, about 35 g) was added to the reaction mixture in a weight ratio of about 1:1 with respect to the epoxy product formed. Excess epichlorohydrin and water were removed using rotary evaporation. Solvent and water were added to the mixture, the mixture was stirred, and the phases were separated. Water washing was repeated twice more to remove more water soluble components. Solvent was removed by rotary evaporation (about 90° C. and about 60 mbara). The sample was then heated in an oven to about 120° C. and stripped with nitrogen for about 30 minutes to afford the glycidyl ether of biological origin.

Example 1E. For this glycidation experiment, a polyhydric phenol of biological origin was used as the substrate (acidified, extracted kraft lignin #3). The substrate was removed from the substrate source (Kraft lignin) by extraction with acidification as described herein and as shown in non-limiting Example 2, below. Water was not removed from the reactor during the reaction.

Synthesis of the glycidyl ethers of Example 1E was performed according to the following procedure. The polyhydric phenol (about 100 g) and a stoichiometric excess of epichlorohydrin (about 500 g) was added to a reactor fitted with an overhead condenser. The resultant mixture was stirred using an overhead stirrer and the reactor was heated to a desired reaction temperature (between about 65° C. and about 75° C.). A coupling catalyst, TMAC (about 50% aqueous, about 8.4 g), was added and a vacuum was applied until the reaction mixture started to boil. Reflux was maintained for about 1 hour to about 3 hours. Sodium hydroxide (about 50% aqueous, about 34.4 g) was then dosed to the reaction mixture over a period of about 4 hours to about 6 hours. The reaction mixture was allowed to continue stirring for about 15 minutes to about 45 minutes of post-reaction time. A liquid epoxy resin (Epikote 862, about 111 g) was added to the reaction mixture in a weight ratio of about 1:1 with respect to the epoxy product formed. Excess epichlorohydrin and solvent was removed by vacuum distillation and the reaction mixture was stripped with nitrogen for about 30 minutes to about 60 minutes. Solvent and water was added to the mixture, the mixture was stirred, and the phases were separated. Water washing was repeated once to remove more water soluble components. Solvent was removed by vacuum distillation and stripping with nitrogen for about 30 minutes to about 60 minutes to afford the glycidyl ether of biological origin.

Selected results from the example glycidations of Examples 1A-1E are shown in Table 1-1. The epoxy group content, hydrolyzable chlorine, and viscosity measurements were taken on the product from the glycidation reaction and include the liquid epoxy resin (LER). The liquid epoxy resin (Epikote 862) utilized in the examples has an epoxy group content of 5,350 mmol/kg, a hydrolyzable chlorine content of less than 300 mg/kg, and a viscosity (@ 40° C.) of 0.59 Pa·s.

TABLE 1-1

| Example No. | Lignin source | Catalyst | Epoxy group content, mmol/kg | Hydrolyzable chlorine content, mg/kg | Viscosity, Pa · s @ 40° C. |
|---|---|---|---|---|---|
| Ex. 1A | extracted lignin #1 | TBAC | 4,330 | — | 659.3 |
| Ex. 1B | extracted lignin #1 | TMAC | 4,272 | — | 678.8 |
| Ex. 1C | acidified extracted lignin #3 | TMAC | 4,700 | — | 7.4 |
| Ex. 1D | acidified extracted lignin #3 | TMAC | 3,750 | 29,230 | 7.8 |
| Ex. 1E | acidified extracted lignin #3 | TMAC | 3,741 | 18,000 | 8.5 |

The data in Table 1-1 indicates that the source of lignin and the extraction method can have a significant effect on the viscosity of the final product. For example, Examples 1A and 1B utilized lignin #1 and were subjected to an epichlorohydrin extraction, whereas Examples 1C, 1D, and 1E utilized lignin #3 and were subjected to an acidified epichlorohydrin extraction (described below). Examples 1A and 1B were determined to have an average epoxy group content (EGC) value of about 4,300 mmol/kg and viscosities (@ 40° C.) of about 659 Pa·s and about 678.8 Pa·s, respectively. In contrast, Examples 1C, 1D, and 1E were determined to have EGC values from about 3,741 mmol/kg to about 4,700 mmol/kg and viscosities (@ 40° C.) from about 7.4 Pa·s to about 8.5 Pa·s. Examples 1A-1E indicated good results for EGC. Such EGC values are commercially viable.

On laboratory scales, and when no liquid epoxy resin is used, the inventors have observed that the products are solids and sticky, viscous globs or balls that are very difficult to remove from a flask or reactor. That is, when a liquid epoxy resin is not used, the product would be a solid or would be of such high viscosity that the product could not be suitably removed from the reactor or flask, and therefore unsuitable for commercial set-up. In contrast, and as described herein, embodiments of the present disclosure utilize a liquid epoxy resin to, for example, prevent (or at least mitigate) gelling or solidification of the epoxy resin product mixture (glycidated product) upon removal of the epihalohydrin. The addition of the liquid epoxy resin can help solubilize, and reduce the viscosity of, the product mixture. The addition of the liquid epoxy resin to the product mixture can also aid in discharging the product mixture from the unit or reactor utilized for the reaction. Further, the addition of the liquid epoxy resin to the product mixture can assist in the removal of salts and brine formed during the glycidation, the removal of by-products formed from the glycidation, the removal of unreacted epihalohydrin, or combinations thereof, among other materials. In such a manner, embodiments described herein enable use of unconventional substrates to be utilized to form epoxy resin compositions.

Without the addition of the LER, the product mixture from the glycidation would gel or solidify as a result of using unconventional substrates, in this case, Kraft lignin. In contrast, the low viscosity of the product can enable easy work-up, transfer to another reactor, among other further uses unavailable to product mixtures not including the LER. Overall, the results indicated that glycidation processes described herein can be used to glycidate unconventional substrates.

The high values of hydrolyzable chlorine may be a result of the difficulty in measuring it, the large error of margin, and that ASTM-D1726 is designed to measure low values down to about 7 mg/kg. Also, by-products present in the product can contribute to the hydrolyzable chlorine content. In addition, a finishing reaction was not performed on these samples.

Example 2: Separation of Substrates from Substrate Sources

Separation of hydroxyl-containing substrates by embodiments described herein were performed using Kraft lignin as the substrate source and epichlorohydrin (ECH) as the epihalohydrin. Three different Kraft lignin samples were obtained from three different commercial vendors. The Kraft lignin substrate source was not depolymerized or pre-reacted in any other way, meaning that high weight average molecular weight (Mw) molecules are present in each sample of Kraft lignin.

Examples 2A-2C. To each Kraft lignin sample (lignin 1, lignin 2, and lignin 3) was added ECH and the resulting mixtures were mixed for about 1 hour at a temperature of about room temperature and a pressure of about atmospheric pressure. A mass ratio of lignin:ECH for each of the three samples was about 1:5. The mixture was filtered by vacuum filtration, and then the ECH was removed by distillation at about 90° C. and a pressure of about 100 mbara (about 10 kPa (absolute)) to provide the separated lignin as the desired substrate.

Each of Examples 2A-2C were repeated in triplicate and selected results from the separations of Examples 2A-2C are shown in Table 2-1. Separation yield as a percentage was determined based on mass by the following equation:

$$(\text{weight of dried extracted substrate/weight of dried substrate source}) \times 100$$

TABLE 2-1

| Example No. | Lignin source | Separation yield, % |
|---|---|---|
| 2A | Lignin 1 | 50 |
| 2B | Lignin 2 | 4 |
| 2C | Lignin 3 | 26 |

At a mass ratio of 1:5 of lignin:ECH, the lignin was observed to be well-dispersed in the ECH. As shown in Table 2-1, about half of the lignin of Example 2A is dissolved in the epichlorohydrin, while significantly lower fractions of lignin dissolve in Examples 2B and 2C. That is, Example 2A showed a separation yield of about 50%, while Examples 2B and 2C showed a separation yield of about 4% and about 26%, respectively. Overall, the results indicated that epihalohydrins can be used to separate desired substrates from the complex Kraft lignin mixtures.

Examples 2D and 2E. Acidification was performed to, for example, increase the separation yield. For these experiments, lignin 2 and lignin 3 were used as the Kraft lignin samples. Acetic acid (about 98%, about 17 M) was utilized. ECH was added to Kraft lignin samples (lignin 2 and lignin 3) at a mass ratio of lignin:ECH of about 1:5 and the resulting mixture was stirred. The acetic acid was then added to the mixture of ECH and lignin, and the resulting mixture was stirred until the pH reached a value of about 2, and was then stirred for about 1 hour at a temperature of about room temperature and a pressure of about atmospheric pressure. The mixture was filtered by vacuum filtration, and then the ECH and acetic acid was removed by distillation at about 90° C. and a pressure of about 100 mbara (about 10 kPa (absolute)) to provide the separated lignin as the desired substrate.

Each of Examples 2D and 2E were repeated in triplicate and selected results from the separations of Examples 2D and 2E are shown in Table 2-2. Separation yield was determined as described above.

TABLE 2-2

| Example No. | Lignin source | Separation yield, % |
|---|---|---|
| 2D | Lignin 2 | 55 |
| 2E | Lignin 3 | 65-70 |

As shown in Table 2-2, use of an acid can significantly improve the separation yield in both cases. Here, the separation yield increased from about 4% to about 55% for lignin 2 (Example 2D) and the separation yield increased from about 26% to a range of about 65% to about 70% (Example 2E). Overall, the results shown in Table 2-2 indicated that acidification can be used to improve separation of desired substrates from the complex Kraft lignin mixtures.

The separation of desired substrates from the Kraft lignin (substrate sources) were also performed on a large scale. While ECH could be removed from the desired lignin substrate using Kraft lignin sources 1 and 3, it was difficult to remove ECH from the desired lignin substrate using Kraft lignin source 2 under the conditions tested. In cases where ECH may be difficult to remove, the mixture of ECH and desired lignin (the filtrate after filtration) can be used directly for glycidation to obtain corresponding epoxy resins.

Embodiments described herein generally relate to processes for forming epoxy resin compositions. The process for forming epoxy resin compositions can be used on unconventional substrates such as substrates of biological origin, as well as waste streams or recycle streams comprising resins. Embodiments of the present disclosure also relate to processes for separating substrates from complex mixtures. The separation processes can enable extraction of glycidation substrates from complex mixtures using an epihalohydrin.

EMBODIMENTS LISTING

The present disclosure provides, among others, the following aspects, each of which can be considered as optionally including any alternate embodiments:

Clause A1. A process for forming an epoxy resin composition, the process comprising:

reacting a mixture comprising a substrate comprising at least one hydroxyl group, an epihalohydrin, and a catalyst to form a first composition comprising a halohydrin reaction product;

introducing an alkaline reagent with the first composition to form a second composition comprising an epoxy resin product, a residual halohydrin reaction product, and a salt;

introducing a liquid epoxy resin with the second composition to form a liquid resin mixture; and removing unreacted epihalohydrin from the liquid resin mixture to form the epoxy resin composition.

Clause A2. The process of Clause A1, wherein, after the removing unreacted epihalohydrin from the liquid resin mixture, the process further comprises: converting at least a portion of any residual halohydrin reaction product in the liquid resin mixture to an epoxy resin.

Clause A3. The process of Clause A1 or Clause A2, wherein the substrate comprising the at least one hydroxyl group comprises an alcohol of biological origin, an alcohol present in a resin waste stream, an alcohol present in a resin recycle stream, or combinations thereof.

Clause A4. The process of Clause A3, wherein the substrate comprises a polyhydric phenol.

Clause A5. The process of Clause A3 or Clause A4, wherein the substrate comprises an aliphatic hydroxyl.

Clause A6. The process of any one of Clauses A1-A5, wherein the substrate comprises a polyhydric phenol, an aliphatic alcohol, or combinations thereof.

Clause A7. The process of any one of Clauses A1-A6, wherein the catalyst is selected from the group consisting of an alkali metal hydroxide, an alkali earth metal hydroxide, an ammonium salt, a phosphonium salt, a sulfonium salt, a lithium salt, and combinations thereof.

Clause A8. The process of any one of Clauses A1-A7, wherein:

the catalyst is selected from the group consisting of sodium hydroxide, potassium hydroxide, calcium hydroxide, tetramethyl ammonium chloride, tetrabutyl ammonium chloride, tetrabutyl ammonium bromide, and combinations thereof;

the alkaline reagent is selected from the group consisting of sodium hydroxide, potassium hydroxide, lithium hydroxide, calcium hydroxide, magnesium hydroxide, and combinations thereof, the catalyst and the alkaline reagent being the same or different; or combinations thereof.

Clause A9. The process of Clause A8, wherein the catalyst and the alkaline reagent are different.

Clause A10. The process of any one of Clauses A1-A9, wherein the epihalohydrin comprises epichlorohydrin.

Clause A11. The process of any one of Clauses A1-A10, wherein the liquid epoxy resin has a viscosity that is about 15 Pa·s or less at 25° C.

Clause B1. A process for making a liquid epoxy resin composition, the process comprising:

reacting a mixture comprising an alcohol of biological origin, an epihalohydrin, and a catalyst to form a first composition comprising a halohydrin reaction product;

introducing an alkaline reagent with the first composition to form a second composition comprising a glycidated product, residual halohydrin reaction product, and a salt;

introducing a liquid epoxy resin with the second composition to form a liquid resin mixture;

removing unreacted epihalohydrin from the liquid resin mixture;

separating the salt from the liquid resin mixture; and forming the liquid epoxy resin composition by:

converting at least a portion of the residual halohydrin reaction product in the liquid resin mixture to an epoxy resin;

performing a liquid-liquid separation of the liquid resin mixture; or combinations thereof.

Clause B2. The process of Clause B1, wherein:

the catalyst is selected from the group consisting of sodium hydroxide, potassium hydroxide, calcium hydroxide, tetramethyl ammonium chloride, tetrabutyl ammonium chloride, tetrabutyl ammonium bromide, and combinations thereof;

the alkaline reagent is selected from the group consisting of sodium hydroxide, potassium hydroxide, lithium hydroxide, calcium hydroxide, magnesium hydroxide, and combinations thereof, the catalyst and the alkaline reagent being the same or different; or combinations thereof.

Clause B3. The process of Clause B2, wherein the catalyst and the alkaline reagent are different.

Clause B4. The process of any one of Clauses B1-B3, wherein the alcohol of biological origin comprises a phenol, an aliphatic hydroxyl, or combinations thereof.

Clause B5. The process of any one of Clauses B1-B4, wherein the alcohol of biological origin comprises a lignin selected from the group consisting of technical lignin, Kraft lignin, organosolv lignin, hydrolysis lignin, or combinations thereof.

Clause B6. The process of any one of Clauses B1-B5, wherein the epihalohydrin is epichlorohydrin.

Clause B7. The process of any one of Clauses B1-B6, wherein the mixture comprises:

a molar ratio of epoxy group of the epihalohydrin to hydroxyl group of the alcohol of biological origin that is from about 1:1 to about 50:1;

a molar ratio of catalyst to hydroxyl group of the alcohol of biological origin that is from about 0.01:1 to about 0.15:1; or combinations thereof.

Clause C1. A process for converting a substrate to a liquid epoxy resin composition, the process comprising:

reacting a mixture comprising the substrate, an epihalohydrin, and a catalyst to form a first composition comprising a halohydrin reaction product and a salt, the substrate comprising an alcohol of biological origin, an alcohol present in a resin waste stream, an alcohol present in a resin recycle stream, or combinations thereof;

introducing an alkaline reagent with the first composition to form a second composition comprising a glycidated product, residual halohydrin reaction product, and a salt;

introducing a liquid epoxy resin with the second composition to form a liquid resin mixture, the liquid epoxy resin having a viscosity that is about 15 Pa·s or less at 25° C.;

removing unreacted epihalohydrin from the liquid resin mixture; and separating the salt from the liquid resin mixture to form the liquid epoxy resin composition.

Clause C2. The process of Clause C1, wherein the substrate is derived from a substrate source by:

introducing the substrate source with an epihalohydrin and separating the substrate and the epihalohydrin from the substrate source; or introducing the substrate source with an epihalohydrin and an acid, and separating the substrate and the epihalohydrin from the substrate source.

Clause D1. A process, comprising:

introducing an epihalohydrin with a substrate source comprising a substrate, the substrate comprising at least one hydroxyl group; and separating the epihalohydrin and the substrate from the substrate source.

Clause D2. The process of Clause D1, further comprising removing the epihalohydrin from the substrate.

Clause D3. The process of Clause D1 or Clause D2, wherein the substrate comprises a phenol, a polyhydric phenol, an aliphatic alcohol, or combinations thereof.

Clause D4. The process of any one of Clauses D1-D3, wherein a mass ratio of the substrate source to the epihalohydrin is from about 1:1 to about 1:10.

Clause D5. The process of any one of Clauses D1-D4, wherein the epihalohydrin comprises epichlorohydrin, epibromohydrin, or combinations thereof.

Clause E1. A process, comprising:

introducing an acid solution and an epihalohydrin with a substrate source comprising a substrate, the substrate comprising at least one hydroxyl group; and separating the epihalohydrin and the substrate from the substrate source.

Clause E2. The process of Clause E1, wherein the acid solution has a pH from about 1 to about 3.

Clause E3. The process of Clause E1 or Clause E2, wherein a mass ratio of the substrate source to the epihalohydrin is from about 1:1 to about 1:10.

Clause E4. The process of any one of Clauses E1-E3, wherein:

a mixture comprising the acid solution, the epihalohydrin, and the substrate source before the separating has a pH that is from about 2 to about 3;

a molarity of the acid solution is from about 0.01 M to about 18M; or combinations thereof.

Clause E5. The process of any one of Clauses E1-E4, wherein a mass ratio of the acid solution to the substrate source is from about 0.1:1 to about 1:1.

Clause E6. The process of any one of Clauses E1-E5, wherein the acid solution comprises acetic acid, hydrochloric acid, oxalic acid, phosphoric acid, p-toluenesulfonic acid, an ion thereof, or combinations thereof.

Clause E7. The process of any one of Clauses E1-E6, wherein the substrate comprising the at least one hydroxyl group comprises a phenol, a polyhydric phenol, an aliphatic alcohol, or combinations thereof.

Clause F1. A process for making an epoxy resin composition, the process comprising:

introducing a first epihalohydrin with a substrate source, the substrate source comprising a substrate, the substrate comprising at least one hydroxyl group;

separating at least a portion of the first epihalohydrin and the substrate from the substrate source; and converting the substrate to the epoxy resin composition.

Clause F2. The process of Clause F1, wherein the converting the substrate to the epoxy resin composition comprises:

reacting a mixture comprising the substrate, a second epihalohydrin, and a catalyst to form a first composition comprising a halohydrin reaction product, the first epihalohydrin and the second epihalohydrin being the same or different; and introducing an alkaline reagent with the first composition to form a second composition comprising an epoxy resin product, a residual halohydrin reaction product, and a salt.

Clause F3. The process of Clause F2, wherein, after the introducing the alkaline reagent with the first composition to form the second composition, the process further comprises:

introducing a liquid epoxy resin with the second composition to form a liquid resin mixture; and removing unreacted epihalohydrin from the liquid resin mixture.

Clause F4. The process of Clause F2 or Clause F3, wherein the second epihalohydrin is fresh epihalohydrin.

Clause F5. The process of any one of Clauses F2-F4, wherein:

each of the first epihalohydrin and the second epihalohydrin is, independently, selected from the group consisting of epichlorohydrin, epibromohydrin, or combinations thereof;

a mass ratio of the substrate source to the first epihalohydrin is from about 1:1 to about 1:10; or combinations thereof.

Clause F6. The process of any one of Clauses F1-F5, further comprising:

introducing an acid solution to the substrate source prior to, during, or after introducing the first epihalohydrin with the substrate source.

Clause F7. The process of Clause F6, wherein:

a mixture comprising the acid solution, the first epihalohydrin, and the substrate source before the separating has a pH that is from about 2 to about 3;

a molarity of the acid solution is from about 0.01 M to about 18M; or combinations thereof.

Clause F8. The process of Clause F6 or Clause F7, wherein a mass ratio of the acid solution to the substrate source is from about 0.01:1 to about 1:1.

As used herein, reference to an R group, alkyl, substituted alkyl, hydrocarbyl, or substituted hydrocarbyl without specifying a particular isomer (such as butyl) expressly discloses all isomers (such as n-butyl, iso-butyl, sec-butyl, and tert-butyl). For example, reference to an R group having 4 carbon atoms expressly discloses all isomers thereof. When a compound is described herein such that a particular isomer, enantiomer or diastereomer of the compound is not specified, for example, in a formula or in a chemical name, that description is intended to include each isomer and enantiomer of the compound described individual or in any combination.

As is apparent from the foregoing general description and the specific aspects, while forms of the aspects have been illustrated and described, various modifications can be made without departing from the spirit and scope of the present disclosure. Accordingly, it is not intended that the present disclosure be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "Is" preceding the recitation of the composition, element, or elements and vice versa, such as the terms "comprising," "consisting essentially of," "consisting of" also include the product of the combinations of elements listed after the term.

For purposes of this present disclosure, and unless otherwise specified, all numerical values within the detailed description and the claims herein are modified by "about" or "approximately" the indicated value, and consider experimental error and variations that would be expected by a person having ordinary skill in the art. For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. For example, the recitation of the numerical range 1 to 5 includes the subranges 1 to 4, 1.5 to 4.5, 1 to 2, among other subranges. As another example, the recitation of the numerical ranges 1 to 5, such as 2 to 4, includes the subranges 1 to 4 and 2 to 5, among other subranges. Additionally, within a range includes every point or individual value between its end points even though not explicitly recited. For example, the recitation of the numerical range 1 to 5 includes the numbers 1, 1.5, 2, 2.75, 3, 3.80, 4, 5, among other numbers. Thus, every point or individual value may serve as its own lower or upper limit combined with any other point or individual value or any other lower or upper limit, to recite a range not explicitly recited.

As used herein, the indefinite article "a" or "an" shall mean "at least one" unless specified to the contrary or the context clearly indicates otherwise. For example, aspects comprising "a catalyst" includes aspects comprising one, two, or more catalysts, unless specified to the contrary or the context clearly indicates only one catalyst is included.

While the foregoing is directed to aspects of the present disclosure, other and further aspects of the disclosure may be devised without departing from the basic scope thereof, and the scope thereof is determined by the claims that follow.

What is claimed is:

1. A process for forming an epoxy resin composition, the process comprising:
- reacting a mixture comprising a substrate comprising at least one hydroxyl group, an epihalohydrin, and a catalyst to form a first composition comprising a halohydrin reaction product;
- introducing an alkaline reagent with the first composition to form a second composition comprising an epoxy resin product, a residual halohydrin reaction product, and a salt;
- introducing a liquid epoxy resin with the second composition to form a liquid resin mixture; and
- removing unreacted epihalohydrin from the liquid resin mixture to form the epoxy resin composition.

2. The process of claim 1, wherein, after the removing unreacted epihalohydrin from the liquid resin mixture, the process further comprises:
- converting at least a portion of any residual halohydrin reaction product in the liquid resin mixture to an epoxy resin.

3. The process of claim 1, wherein the substrate comprising the at least one hydroxyl group comprises an alcohol of biological origin, an alcohol present in a resin waste stream, an alcohol present in a resin recycle stream, or combinations thereof.

4. The process of claim 3, wherein the substrate comprises a polyhydric phenol.

5. The process of claim 3, wherein the substrate comprises an aliphatic hydroxyl.

6. The process of claim 1, wherein the substrate comprises a polyhydric phenol, an aliphatic alcohol, or combinations thereof.

7. The process of claim 1, wherein the catalyst is selected from the group consisting of an alkali metal hydroxide, an alkali earth metal hydroxide, an ammonium salt, a phosphonium salt, a sulfonium salt, a lithium salt, and combinations thereof.

8. The process of claim 1, wherein:
- the catalyst is selected from the group consisting of sodium hydroxide, potassium hydroxide, calcium hydroxide, tetramethyl ammonium chloride, tetrabutyl ammonium chloride, tetrabutyl ammonium bromide, and combinations thereof; and
- the alkaline reagent is selected from the group consisting of sodium hydroxide, potassium hydroxide, lithium hydroxide, calcium hydroxide, magnesium hydroxide, and combinations thereof, the catalyst and the alkaline reagent being the same or different.

9. The process of claim 8, wherein the catalyst and the alkaline reagent are different.

10. The process of claim 1, wherein the epihalohydrin comprises epichlorohydrin.

11. The process of claim 1, wherein the liquid epoxy resin has a viscosity that is about 15 Pa·s or less at 25° C.

12. A process for making a liquid epoxy resin composition, the process comprising:
- reacting a mixture comprising an alcohol of biological origin, an epihalohydrin, and a catalyst to form a first composition comprising a halohydrin reaction product;
- introducing an alkaline reagent with the first composition to form a second composition comprising a glycidated product, residual halohydrin reaction product, and a salt;
- introducing a liquid epoxy resin with the second composition to form a liquid resin mixture;
- removing unreacted epihalohydrin from the liquid resin mixture;
- separating the salt from the liquid resin mixture; and
- after the separating the salt from the liquid resin mixture, forming the liquid epoxy resin composition by:
  - converting at least a portion of the residual halohydrin reaction product in the liquid resin mixture to an epoxy resin;
  - performing a liquid-liquid separation of the liquid resin mixture; or
  - combinations thereof.

13. The process of claim 12, wherein:
- the catalyst is selected from the group consisting of sodium hydroxide, potassium hydroxide, calcium hydroxide, tetramethyl ammonium chloride, tetrabutyl ammonium chloride, tetrabutyl ammonium bromide, and combinations thereof; and
- the alkaline reagent is selected from the group consisting of sodium hydroxide, potassium hydroxide, lithium hydroxide, calcium hydroxide, magnesium hydroxide, and combinations thereof, the catalyst and the alkaline reagent being the same or different.

14. The process of claim 13, wherein the catalyst and the alkaline reagent are different.

15. The process of claim 12, wherein the alcohol of biological origin comprises a phenol, an aliphatic hydroxyl, or combinations thereof.

16. The process of claim 12, wherein the alcohol of biological origin comprises a lignin selected from the group consisting of technical lignin, Kraft lignin, organosolv lignin, hydrolysis lignin, or combinations thereof.

17. The process of claim 12, wherein the epihalohydrin is epichlorohydrin.

18. The process of claim 12, wherein the mixture comprises:

a molar ratio of epoxy group of the epihalohydrin to hydroxyl group of the alcohol of biological origin that is from about 1:1 to about 50:1; and a molar ratio of catalyst to hydroxyl group of the alcohol of biological origin that is from about 0.01:1 to about 0.15:1.

19. A process for converting a substrate to a liquid epoxy resin composition, the process comprising:

reacting a mixture comprising the substrate, an epihalohydrin, and a catalyst to form a first composition comprising a halohydrin reaction product and a salt, the substrate comprising an alcohol of biological origin, an alcohol present in a resin waste stream, an alcohol present in a resin recycle stream, or combinations thereof;

introducing an alkaline reagent with the first composition to form a second composition comprising a glycidated product, residual halohydrin reaction product, and a salt;

introducing a liquid epoxy resin with the second composition to form a liquid resin mixture, the liquid epoxy resin having a viscosity that is about 15 Pa·s or less at 25° C.;

removing unreacted epihalohydrin from the liquid resin mixture; and separating the salt from the liquid resin mixture to form the liquid epoxy resin composition.

20. The process of claim 19, wherein the substrate is derived from a substrate source by:

introducing the substrate source with an epihalohydrin and separating the substrate and the epihalohydrin from the substrate source; or introducing the substrate source with an epihalohydrin and an acid, and separating the substrate and the epihalohydrin from the substrate source.

21. A process for forming an epoxy resin composition, the process comprising:

reacting a mixture comprising a substrate comprising at least one hydroxyl group, an epihalohydrin, and a catalyst to form a first composition comprising a halohydrin reaction product;

introducing an alkaline reagent with the first composition to form a second composition comprising an epoxy resin product, a residual halohydrin reaction product, and a salt;

introducing a liquid epoxy resin with the second composition to form a liquid resin mixture, the liquid epoxy resin having a viscosity that is about 15 Pa·s or less at 25° C.; and removing unreacted epihalohydrin from the liquid resin mixture to form the epoxy resin composition.

* * * * *